Figure 1:
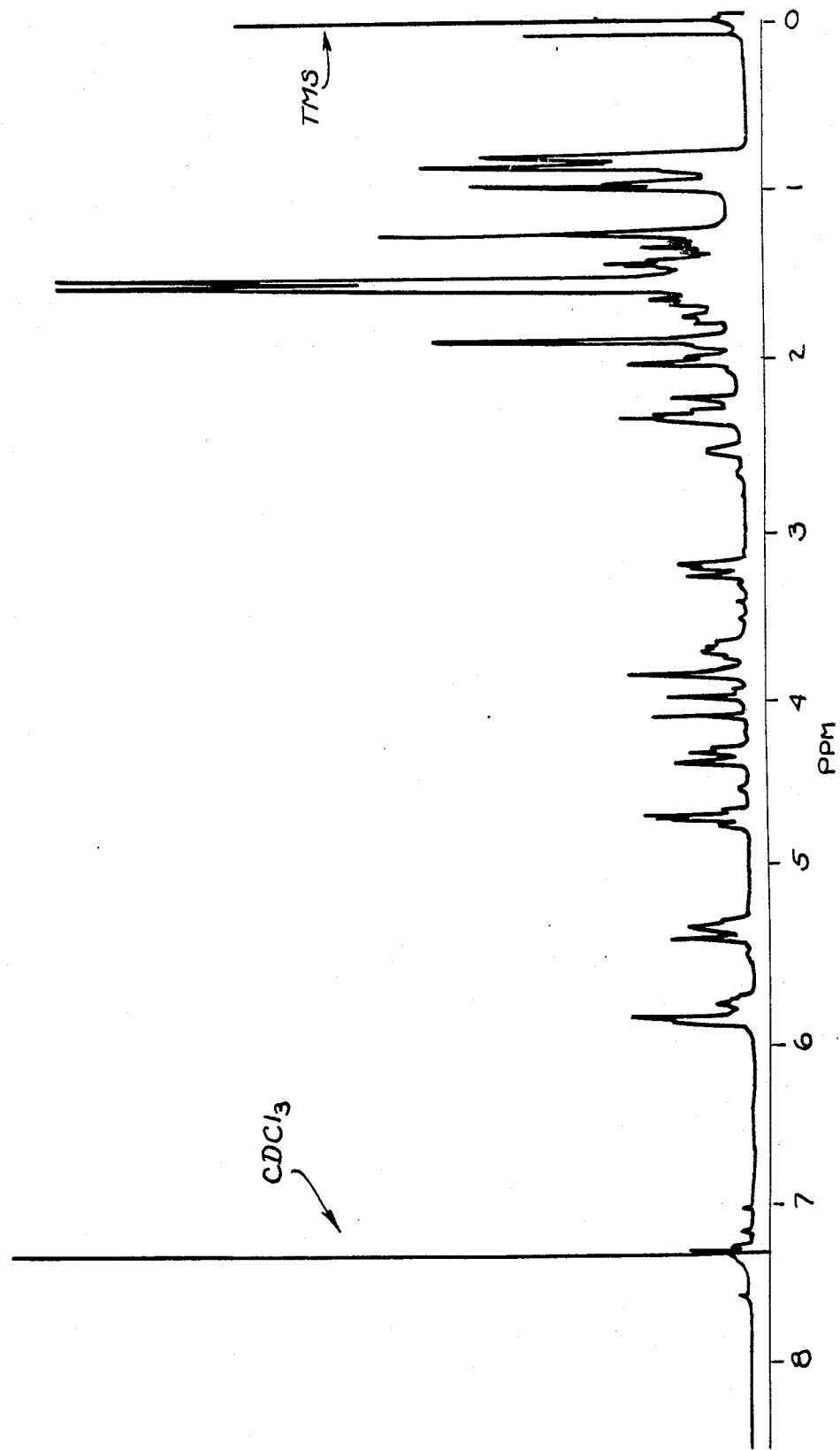

United States Patent [19]

Goegelman et al.

[11] Patent Number: 4,666,937
[45] Date of Patent: May 19, 1987

[54] AVERMECTIN BIOCONVERSION PRODUCTS

[75] Inventors: Robert T. Goegelman, Linden; Edward S. Inamine, Rahway; Raymond F. White, Englishtown, all of N.J.

[73] Assignee: Merck & Co., Inc., Rahway, N.J.

[21] Appl. No.: 830,333

[22] Filed: Feb. 20, 1986

Related U.S. Application Data

[63] Continuation-in-part of Ser. No. 708,194, Mar. 4, 1985.

[51] Int. Cl.$^4$ .................. C07D 493/22; A61K 31/365
[52] U.S. Cl. ...................... 514/450; 549/264; 435/119; 435/253; 435/822
[58] Field of Search .................. 514/450; 549/264; 536/17

[56] References Cited

U.S. PATENT DOCUMENTS

| | | | |
|---|---|---|---|
| 4,199,569 | 4/1980 | Chabala et al. | 514/450 |
| 4,206,205 | 6/1980 | Mrozik et al. | 514/450 |
| 4,310,519 | 1/1982 | Albers-Schonberg et al. | 514/450 |
| 4,530,921 | 7/1985 | Mrozik | 514/450 |
| 4,582,852 | 4/1986 | Gehret | 514/450 |

FOREIGN PATENT DOCUMENTS

| | | | |
|---|---|---|---|
| 0001689 | 5/1979 | European Pat. Off. | 549/264 |
| 0120589 | 7/1982 | Japan | 549/264 |
| 36682 | 2/1984 | Japan | 514/450 |

*Primary Examiner*—Albert T. Meyers
*Assistant Examiner*—Dara Dinner
*Attorney, Agent, or Firm*—David L. Rose; Michael C. Sudol, Jr.

[57] ABSTRACT

There are disclosed novel compounds which are derived from 22,23-dihydro avermectin B1a aglycone, 13-deoxy-22,23 dihydro overmectin B1a aglycone and 13-deoxy-22,23-dihydro overmectin B1b aglycone. The six compounds are hydroxy adducts of the substrate avermectin compound at the 12a, 24, 24a, 26, 26a and 27 positions. The hydroxy adducts are prepared by incubating the substrate with the microorganism *Cunninghamella blakesleeana* and isolating the hydroxy adducts from the fermentation broth. The compounds are highly potent antiparasitic, insecticidal and anthelmintic agents.

15 Claims, 27 Drawing Figures

FIG. II

AVERMECTIN BIOCONVERSION PRODUCTS

CROSS-REFERENCE TO RELATED APPLICATIONS

This application is a continuation-in-part of our co-pending application Ser. No. 708,194, filed Mar. 4, 1985.

BACKGROUND OF THE INVENTION

Avermectin compounds are known antiparasitic agents of considerable activity. The basic material products are described in U.S. Pat. No. 4,310,519. The 22,23-dihydro derivatives are disclosed in U.S. Pat. No. 4,199,569. The monosaccharide and aglycone derivatives are disclosed in U.S. Pat. No. 4,206,205. The 13-deoxy avermectin compounds are disclosed in Re 32034 and Re 32006. The instant hydroxy adducts are significantly different from such compounds.

SUMMARY OF THE INVENTION

The instant invention is concerned with the bioconversion of avermectin compounds into hydroxy adducts. Thus, it is an object of this disclosure to describe such compounds. It is a further object to describe the microorganism used to prepare such compounds and the fermentation conditions applicable to such bioconversion. A still further object of this disclosure is to describe the antiparasitic uses of such bioconversion products and compositions therefor. Further objects will become apparent from reading the following description.

DESCRIPTION OF THE INVENTION

In accordance with this invention, novel substances are described which are prepared by growing under controlled conditions a strain of microorganism identified as *Cunninghamella blakesleeana* and including in the fermentation broth a substrate which is an avermectin compound. This microorganism is identified in the Merck Culture Collection as MF-4415 and is publicly available from the American Type Culture Collection at 12301 Parklawn Drive, Rockville, MD 20852 under the accession number ATCC 8688a. The culture is described in The American Type Culture Collection *Catalogue of Strains I*, 15th Edition (1982) and in *Applied Microbiology* 3, pp. 14–20 (1955).

The instant compounds are produced during the aerobic fermentation of suitable aqueous nutrient media under conditions described hereinafter, with a producing strain of *Cunninghamella blakesleeana* MF-4415, ATCC 8688a. Aqueous media such as those used for the production of many antibiotic substances are suitable for use in the process for the production of these macrocyclic compounds.

Such nutrient media contain sources of carbon and nitrogen assimilable by the microorganism and generally low levels of inorganic salts. In addition, the fermentation media may contain traces of metals necessary for the growth of the microorganisms, and production of the desired compound. These are usually present in sufficient concentrations in the complex sources of carbon and nitrogen, which may be used as nutrient sources, but can, of course, be added separately to the medium if desired.

In general, carbohydrates such as sugars, for example dextrose, sucrose, maltose, lactose, dextran, cerelose, corn meal, oat flour, and the like, and starches are suitable sources of assimilable carbon in the nutrient media.

The exact quantity of the carbon source which is utilized in the medium will depend, in part, upon the other ingredients in the medium, but it is usually found that an amount of carbohydrate between 1 and 10 g/l in the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by *Cunninghamella blakesleeana* MF-4415, ATCC 8688a in the production of the instant compounds. The various sources of nitrogen can be used alone or in combination in amounts ranging from 1 to 5 g/l in the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, and the like.

It should be noted that the media described hereinbelow and in the Examples are merely illustrative of the wide variety of media, which may be employed, and are not intended to be limitative.

The following are Examples of media suitable for growing strains of *Cunninghamella blakesleeana* MF-4415, ATCC 8688a.

|  | g/l |
|---|---|
| Growth Medium 1 | |
| Glucose | 10 |
| Polypeptone | 2 |
| Beef extract | 1 |
| Corn steep liquor | 3 |
| H$_2$O | q.s. |
| pH 7.0 | |
| Growth Medium 2 | |
| Glucose | 4 |
| Yeast extract | 4 |
| Malt extract | 10 |
| H$_2$O | q.s |
| pH 7.0 | |
| Growth Medium 3 | |
| Glucose | 10 |
| KH$_2$PO$_4$ | 1 |
| (NH$_4$)$_2$SO$_4$ | 1 |
| Urea | 0.5 |
| MgSO$_4$.7H$_2$O | 0.5 |
| Yeast extract | 1 |
| H$_2$O | q.s. |
| pH 7.0 | |

The fermentation employing *Cunninghamella blakesleeana* MF-4415, ATCC 8688a can be conducted at temperatures ranging from about 20° C. to about 40° C. For optimum results, it is most convenient to conduct these fermentations at a temperature in the range of from about 24° C. to about 30° C. Temperatures of about 27°–28° C. are most preferred. The pH of the nutrient medium suitable for producing the instant compounds can vary from about 5.0 to 8.5 with a preferred range of from about 6.0 to 7.5.

Small scale fermentations are conveniently carried out by placing suitable quantities of nutrient medium in a flask employing known sterile techniques, inoculating the flask with either spores or vegetative cellular growth of *Cunninghamella blakesleeana* MF-4415, ATCC 8688a loosely stoppering the flask with cotton and permitting the fermentation to proceed in a constant room temperature of about 28° C. on a rotary shaker at from 95 to 300 rpm for about 2 to 10 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of *Cunninghamella blakesleeana* MF-4415, ATCC 8688a. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 300 rpm and about 2 to 20 cubic feet per minute (CFM) of air.

The separation of the novel compound from the whole fermentation broth and the recovery of said compounds is carried out by solvent extraction and application of chromatographic fractionations with various chromatographic techniques and solvent systems.

The instant compounds have slight solubility in water, but is soluble in organic solvents. This property may be conveniently employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extractions are desirable to achieve maximum recovery. The solvent removes the instant compound as well as other substances lacking the antiparasitic activity of the instant compound. If the solvent is a water immiscible one, the layers are separated and the organic solvent is evaporated under reduced pressure. The residue is placed onto a chromatography column containing preferably, silica gel. The column retains the desired products and some impurities, but lets many of the impurities, particularly the nonpolar impurities, pass through. The column is washed with a moderately polar organic solvent such as methylene chloride or chloroform to further remove impurities, and is then washed with a mixture of methylene chloride or chloroform and an organic solvent of which acetone, methanol, and ethanol and the like are preferred. The solvent is evaporated and the residue further chromatographed using column chromatography, thin layer chromatography, preparative thin layer chromatography, high pressure liquid chromatography and the like, with silica gel, aluminum oxide, ion exchange resins, dextran gels and the like, as the chromatographic medium, with various solvents and combinations of solvents as the eluent. Thin layer, high pressure, liquid and preparative thin layer chromatography may be employed to detect the presence of, and to isolate the instant compound. The use of the foregoing techniques as well as others known to those skilled in the art, will afford purified compositions containing the instant compound. The presence of the desired compound is determined by analyzing the various chromatographic fractions for biological activity or physico-chemical characteristics. The structures of the instant compound has been determined by detailed analysis of the various spectral characteristics of the compounds, in particular their nuclear magnetic resonance, mass, ultraviolet and infrared spectra.

The following data characterize six bioconversion products from 22,23-dihydro avermectin B1a aglycone which were isolated from *Cunninghamella blakesleeana*.

Mass Spectral Data

Low resolution mass spectra were recorded on a Finnigan-MAT212 mass spectrometer in the electron impact mode (EI, 90 eV). Exact mass measurements were made on the same instrument at high resolution by the peak matching method using perfluorokerosene (PFK) as internal standard. In each case, the molecular ion was clearly observed and the following HR-MS values were obtained:

| Structure | Found | Calculated | Formula |
|---|---|---|---|
| 1 | 602.3455 | 602.3455 | $C_{34}H_{50}O_9$ |
| 2 | 602.3455 | 602.3455 | $C_{34}H_{50}O_9$ |
| 3 | 602.3455 | 602.3455 | $C_{34}H_{50}O_9$ |
| 4 | 602.3455 | 602.3455 | $C_{34}H_{50}O_9$ |
| 5 | 602.3455 | 602.3455 | $C_{34}H_{50}O_9$ |

$^1$H-NMR Spectra

Figure 2:
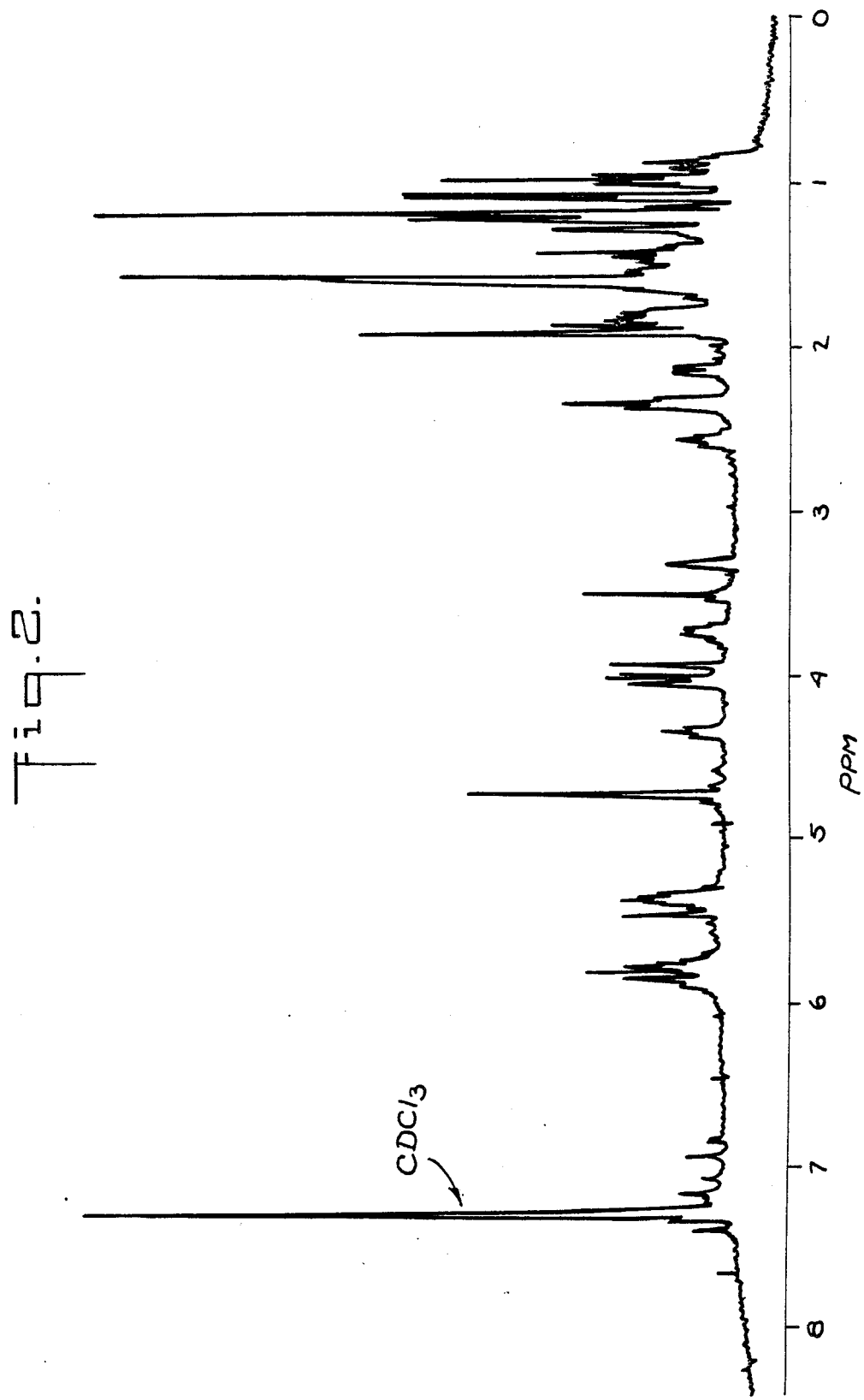
Figure 3:
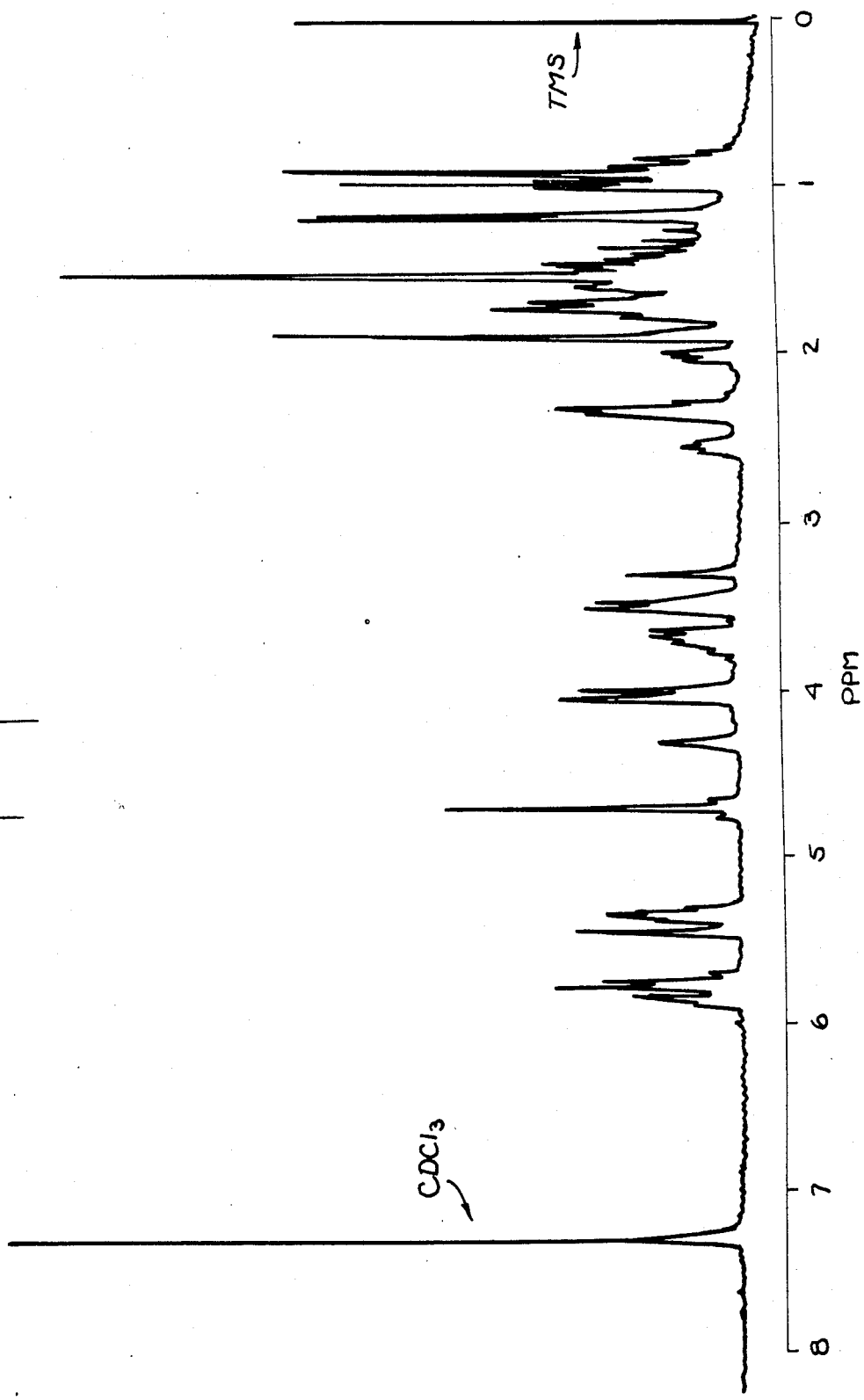
Figure 4:
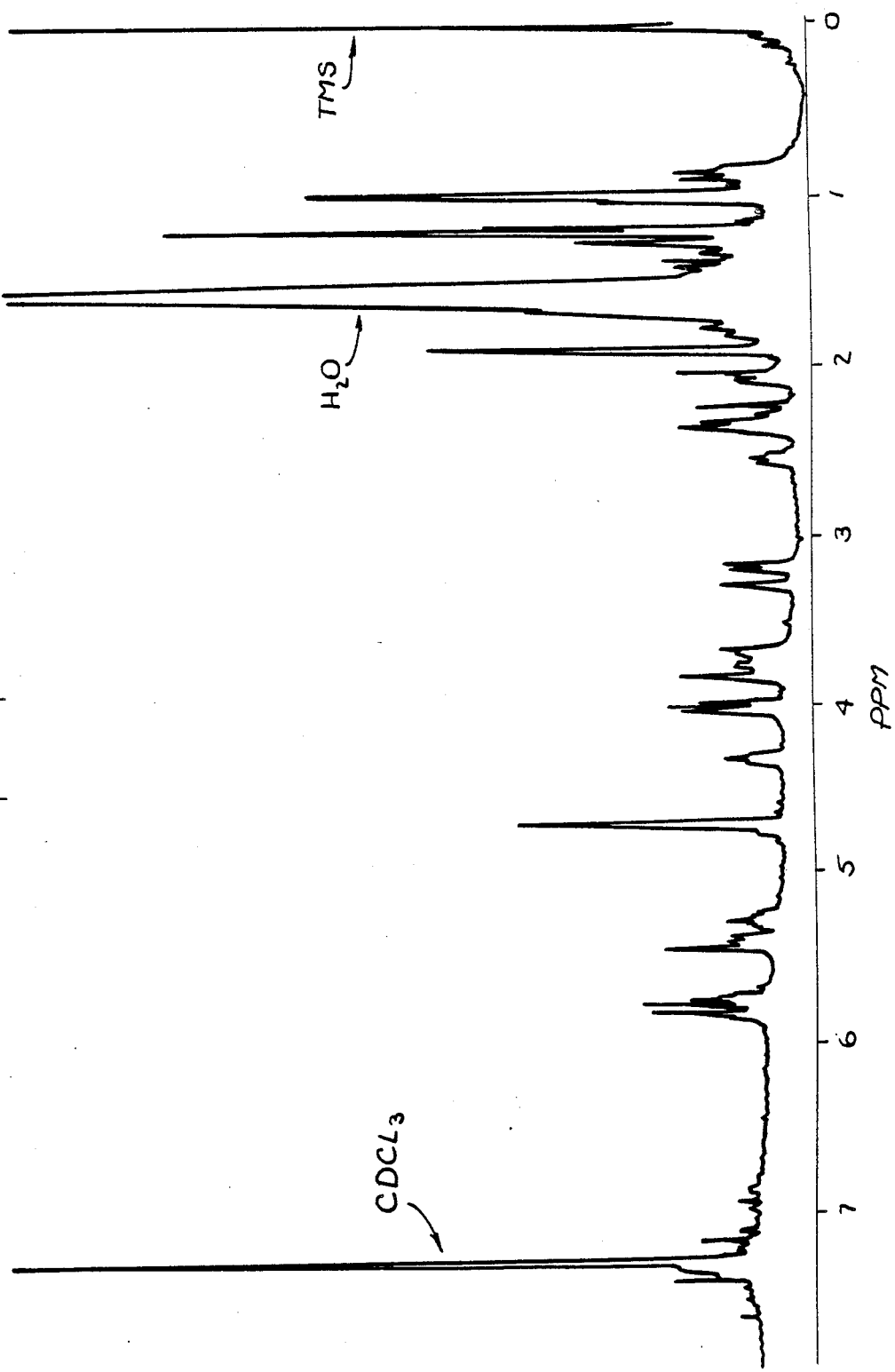
Figure 5:
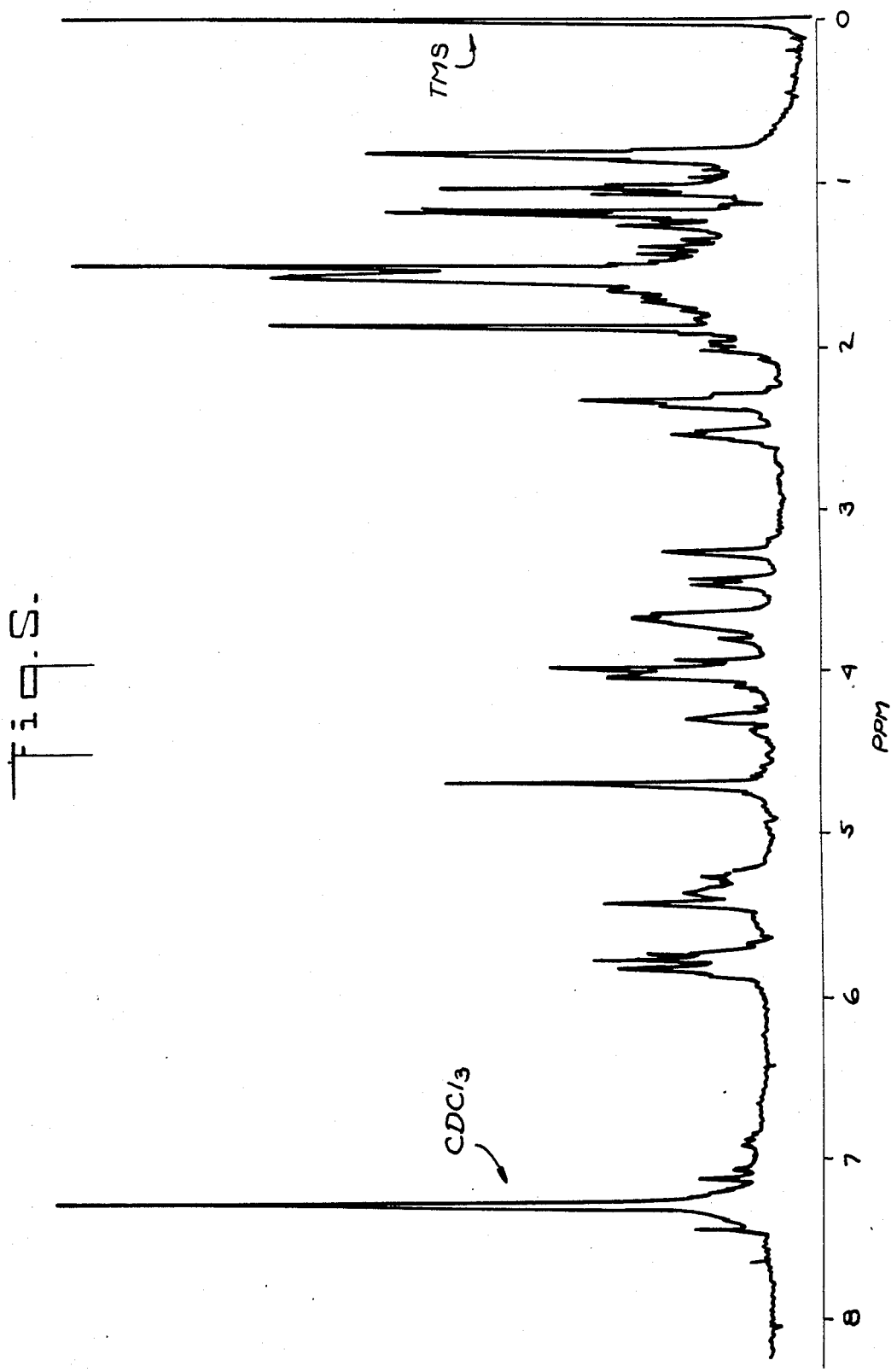
Figure 6:
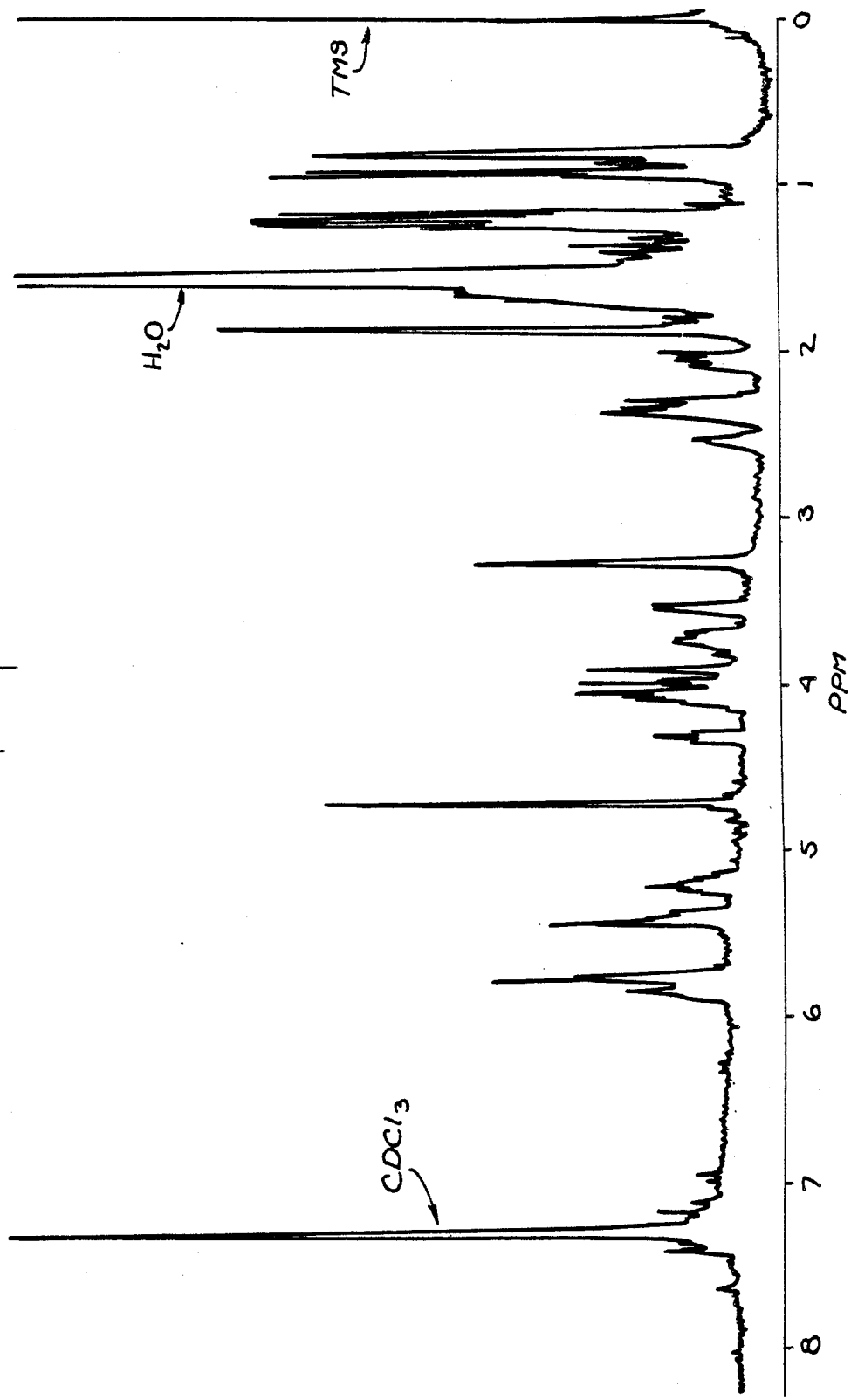

A true copy of the spectrum of each compound is attached hereto as FIGS. 1–6. The spectra were recorded in CDCl$_3$ at ambient temperature on Varian SC-300 and XL-400 NMR spectrometers. Chemical shifts are shown in ppm relative to internal tetramethylsilane at zero ppm.

On the basis of the above and other evidence the assigned structures are shown below (structures 1 to 6).

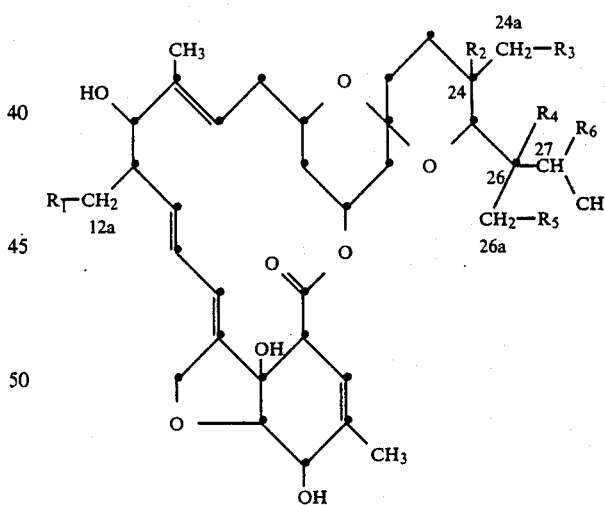

wherein $R_1$, $R_2$, $R_3$, $R_4$, $R_5$ and $R_6$ each may be hydrogen or hydroxy such that only one of such groups is hydroxy at any one time, as is shown in the following table.

| Structure | Name | $R_1$ | $R_2$ | $R_3$ | $R_4$ | $R_5$ | $R_6$ |
|---|---|---|---|---|---|---|---|
| 1 | 12a-hydroxy-22,23-dihydro avermectin B1a aglycone | OH | H | H | H | H | H |
| 2 | 24-hydroxy-22,23-dihydro avermectin B1a aglycone | H | OH | H | H | H | H |
| 3 | 24a-hydroxy-22,23- | H | H | OH | H | H | H |

-continued

| Structure | Name | $R_1$ | $R_2$ | $R_3$ | $R_4$ | $R_5$ | $R_6$ |
|---|---|---|---|---|---|---|---|
|  | dihydro avermectin B1a aglycone |  |  |  |  |  |  |
| 4 | 26-hydroxy-22,23-dihydro avermectin B1a aglycone | H | H | H | OH | H | H |
| 5 | 26a-hydroxy-22,23-dihydro avermectin B1a aglycone | H | H | H | H | OH | H |
| 6 | 27-hydroxy-22,23-dihydro avermectin B1a aglycone | H | H | H | H | H | OH |

It is also recognized that additional substrates may be employed in the fermentation of *Cunninghamella blakesleeana* which are also converted into the hydroxylated derivatives thereof. In particular compounds wherein the 13-position hydroxy is replaced by hydrogen with the 25-position substituent is either sec-butyl or isopropyl are particularly advantageous.

In one such example 13-deoxy-22,23-dihydro avermectin B1a aglycone was used as the substrate and twelve products were recovered. Four of the products were of the same structure as compounds 1, 4, 5, and 6 above, however, the 13-position hydroxy is inverted from the original avermectin substrate. This inversion is identified as "epi-hydroxy". These hydroxy and dihydroxy compounds are identified in the following structural formula and table:

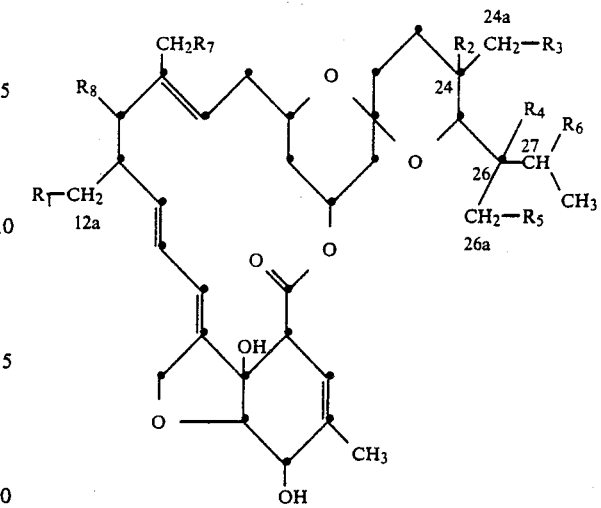

wherein $R_1$, $R_2$, $R_3$, $R_4$, $R_5$, $R_6$, $R_7$ and $R_8$ are as identified in the following table:

| Structure | Name | $R_1$ | $R_2$ | $R_3$ | $R_4$ | $R_5$ | $R_6$ | $R_7$ | $R_8$ |
|---|---|---|---|---|---|---|---|---|---|
| 7 | 13-epi-12a-dihydroxy-22,23-dihydro avermectin B1a aglycone | OH | H | H | H | H | H | H | OH(epi) |
| 8 | 13-epi-14a-dihydroxy-22,23-dihydro avermectin B1a aglycone | H | H | H | H | H | H | OH | OH(epi) |
| 9 | 13-epi-24a-dihydroxy-22,23-dihydro avermectin B1a aglycone | H | H | OH | H | H | H | H | OH(epi) |
| 10 | 13-epi-26-dihydroxy-22,23-dihydro avermectin B1a aglycone | H | H | H | OH | H | H | H | OH(epi) |
| 11 | 13-epi-27-dihydroxy-22,23-dihydro avermectin B1a aglycone | H | H | H | H | H | OH | H | OH(epi) |
| 12 | 13-deoxy-12a-hydroxy-22,23-dihydro avermectin B1a aglycone | OH | H | H | H | H | H | H | H |
| 13 | 13-deoxy-26-hydroxy-22,23-dihydro avermectin B1a aglycone | H | H | H | OH | H | H | H | H |
| 14 | 13-deoxy-26a-hydroxy-22,23-dihydro avermectin B1a aglycone | H | H | H | H | OH | H | H | H |
| 15 | 13-deoxy-12a,24-dihydroxy-22,23-dihydro avermectin B1a aglycone | OH | H | OH | H | H | H | H | H |
| 16 | 13-deoxy-12a,26-dihydroxy-22,23-dihydro avermectin B1a aglycone | OH | H | H | OH | H | H | H | H |
| 17 | 13-deoxy-12a,26a-dihydroxy-22,23-dihydro avermectin B1a aglycone | OH | H | H | H | OH | H | H | H |
| 18 | 13-deoxy-12a,27-dihydroxy-22,23-dihydro avermectin B1a aglycone | OH | H | H | H | H | OH | H | H |

High resolution mass spectrometry data for the foregoing twelve compounds are as follows:

| Structure | Found | Calcd | For | Assignment |
|---|---|---|---|---|
| 7 | 602.3449 | 602.3455 | $C_{34}H_{50}O_9$ | $M^+$ |
| 8 | 602.3437 | 602.3455 | $C_{34}H_{50}O_9$ | $M^+$ |
| 9 | 602.3437 | 602.3455 | $C_{34}H_{50}O_9$ | $M^+$ |
| 10 | 602.3437 | 602.3455 | $C_{34}H_{50}O_9$ | $M^+$ |
| 11 | 602.3437 | 602.3455 | $C_{34}H_{50}O_9$ | $M^+$ |
| 12 | 586.3494 | 586.3506 | $C_{34}H_{50}O_8$ | $M^+$ |
| 13 | 586.3507 | 586.3506 | $C_{34}H_{50}O_8$ | $M^+$ |
| 14 | 586.3507 | 586.3494 | $C_{34}H_{50}O_8$ | $M^+$ |

-continued

| Structure | Found | Calcd | For | Assignment |
|---|---|---|---|---|
| 15 | 602.3444 | 602.3455 | $C_{34}H_{50}O_9$ | $M^+$ |
| 16 | 602.3443 | 602.3455 | $C_{34}H_{50}O_9$ | $M^+$ |
| 17 | 602.3437 | 602.3455 | $C_{34}H_{50}O_9$ | $M^+$ |
| 18 | 602.3450 | 602.3455 | $C_{34}H_{50}O_9$ | $M^+$ |

Figure 7:
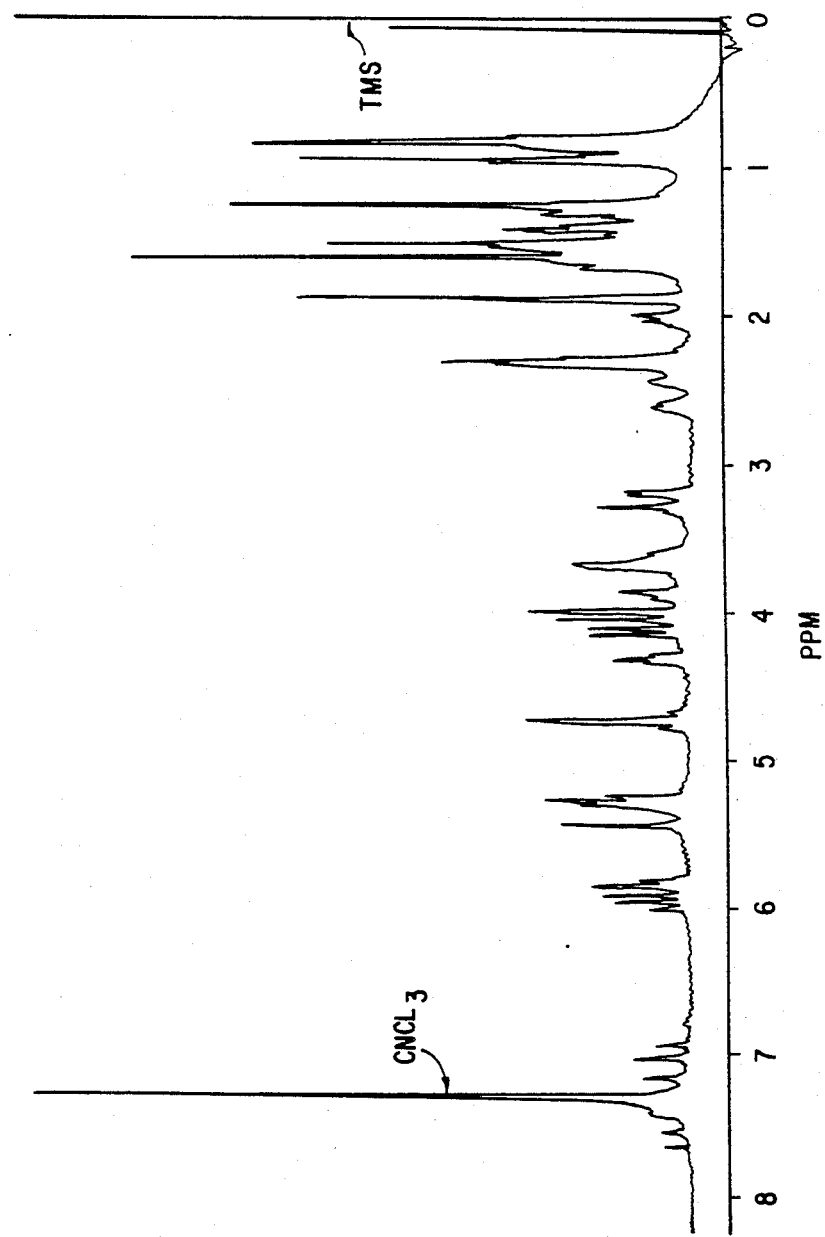
Figure 8:
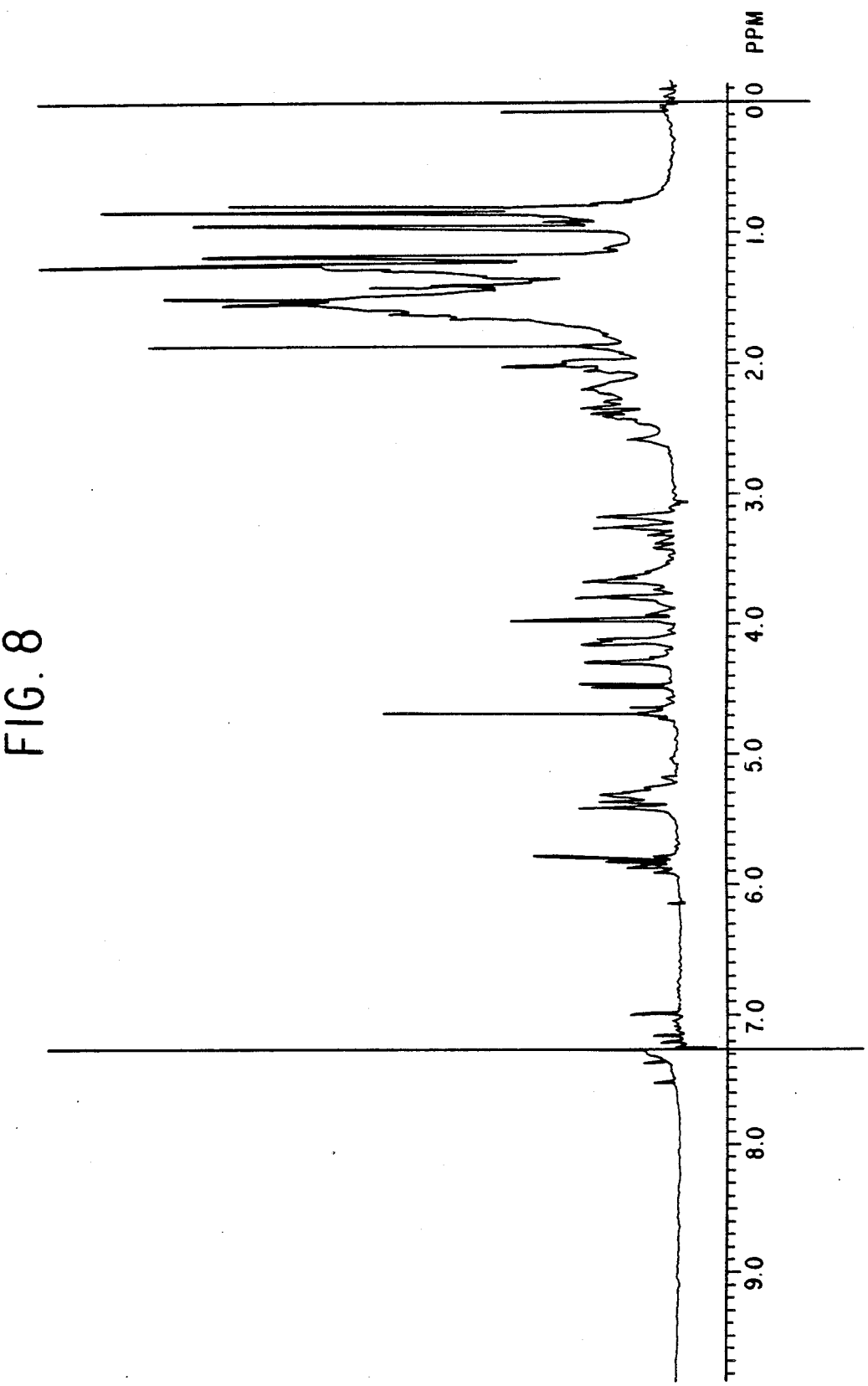
Figure 9:
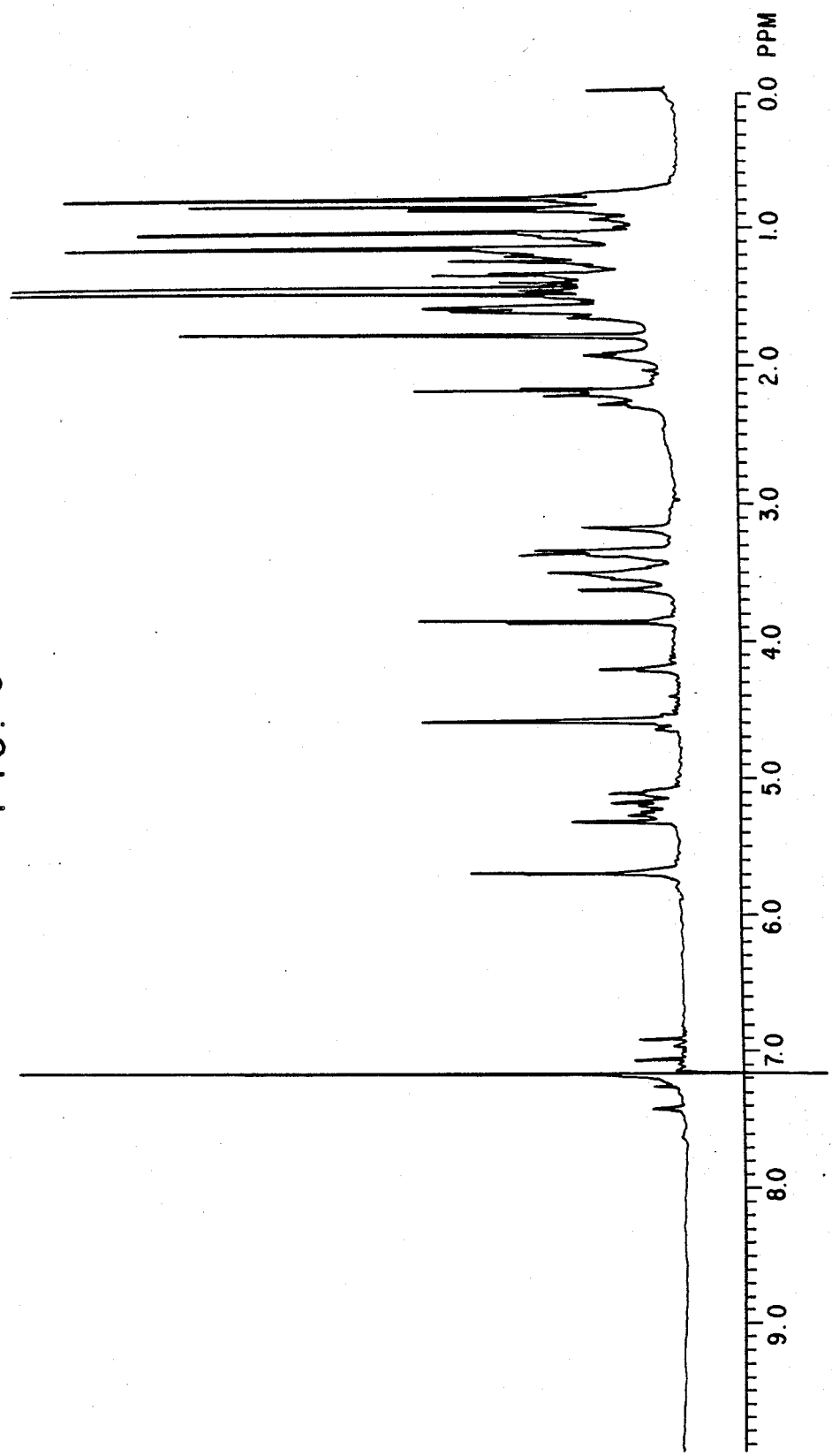
Figure 10:
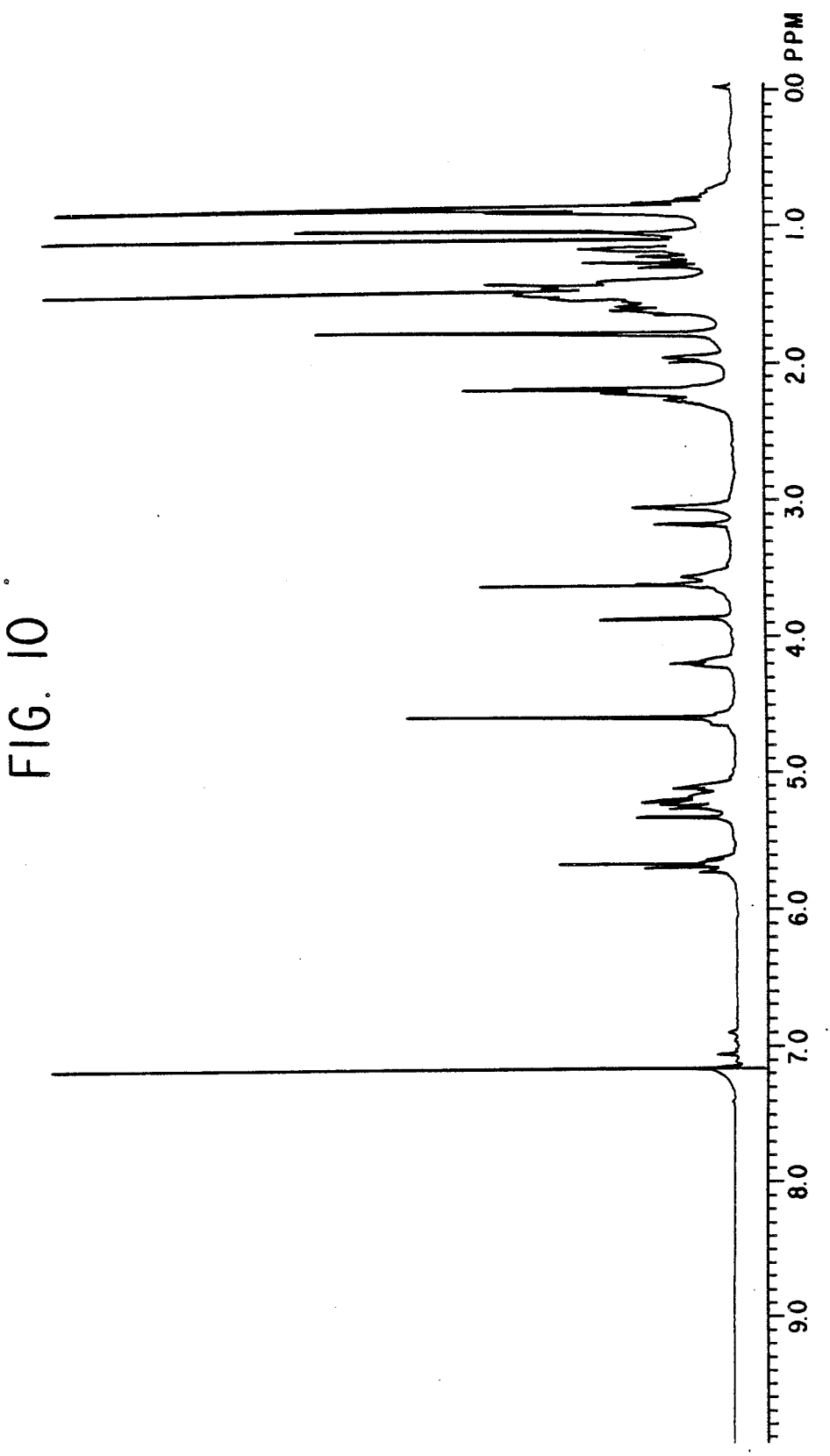
Figure 11:
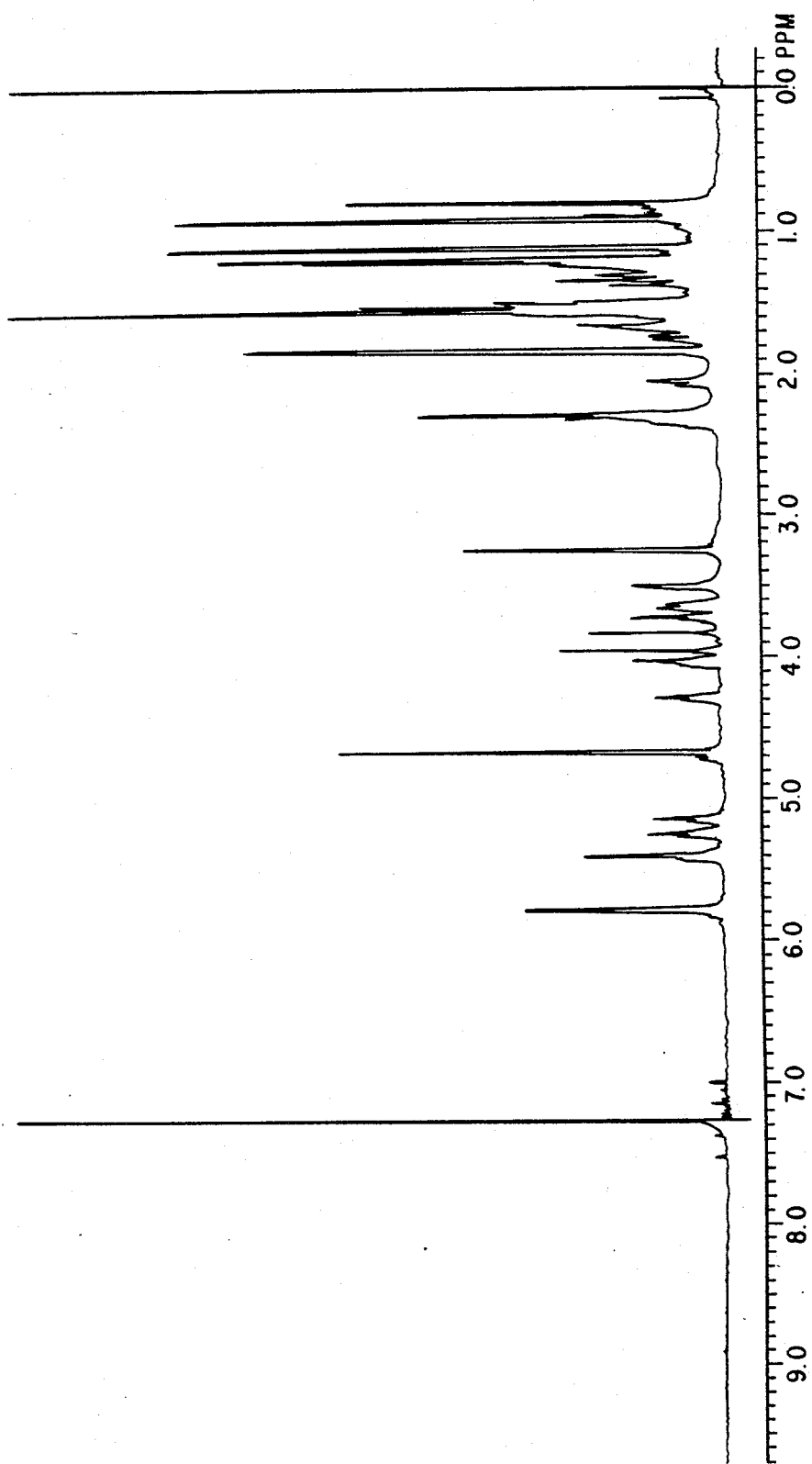
Figure 12:
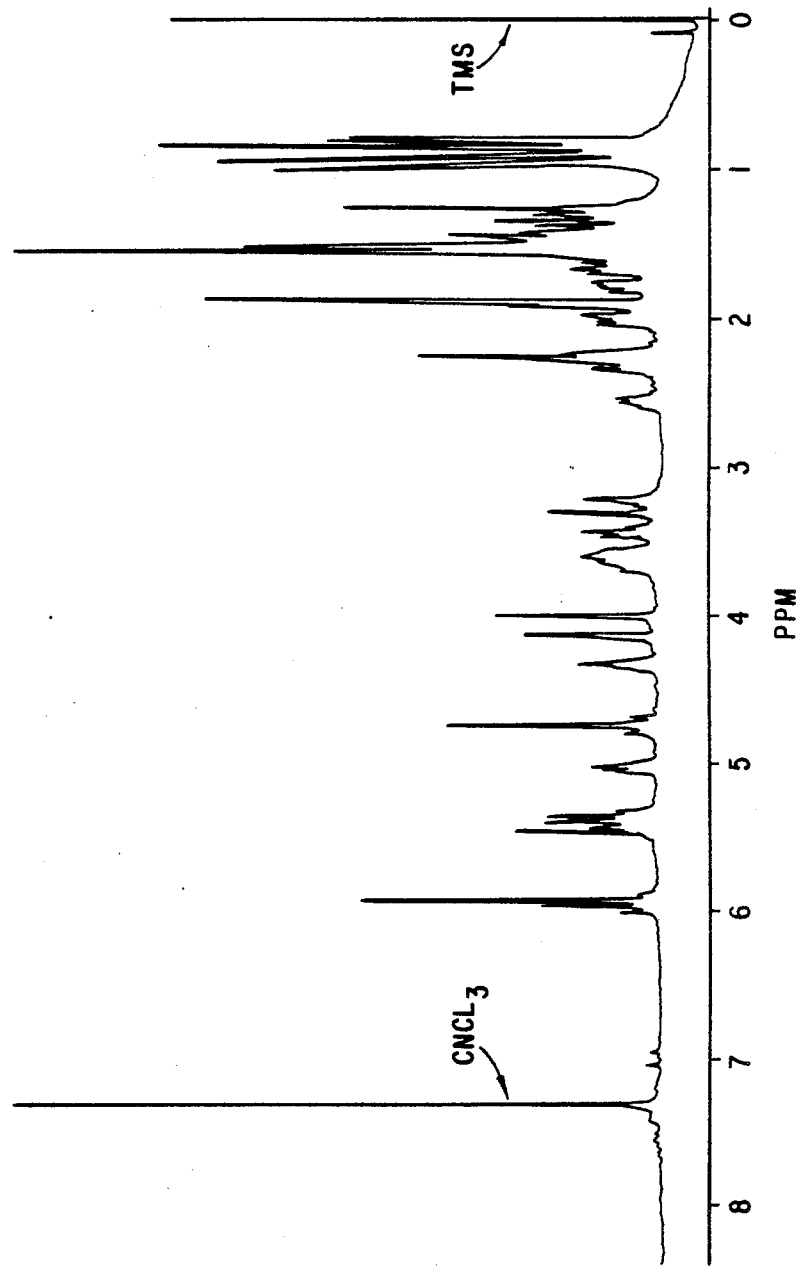
Figure 13:
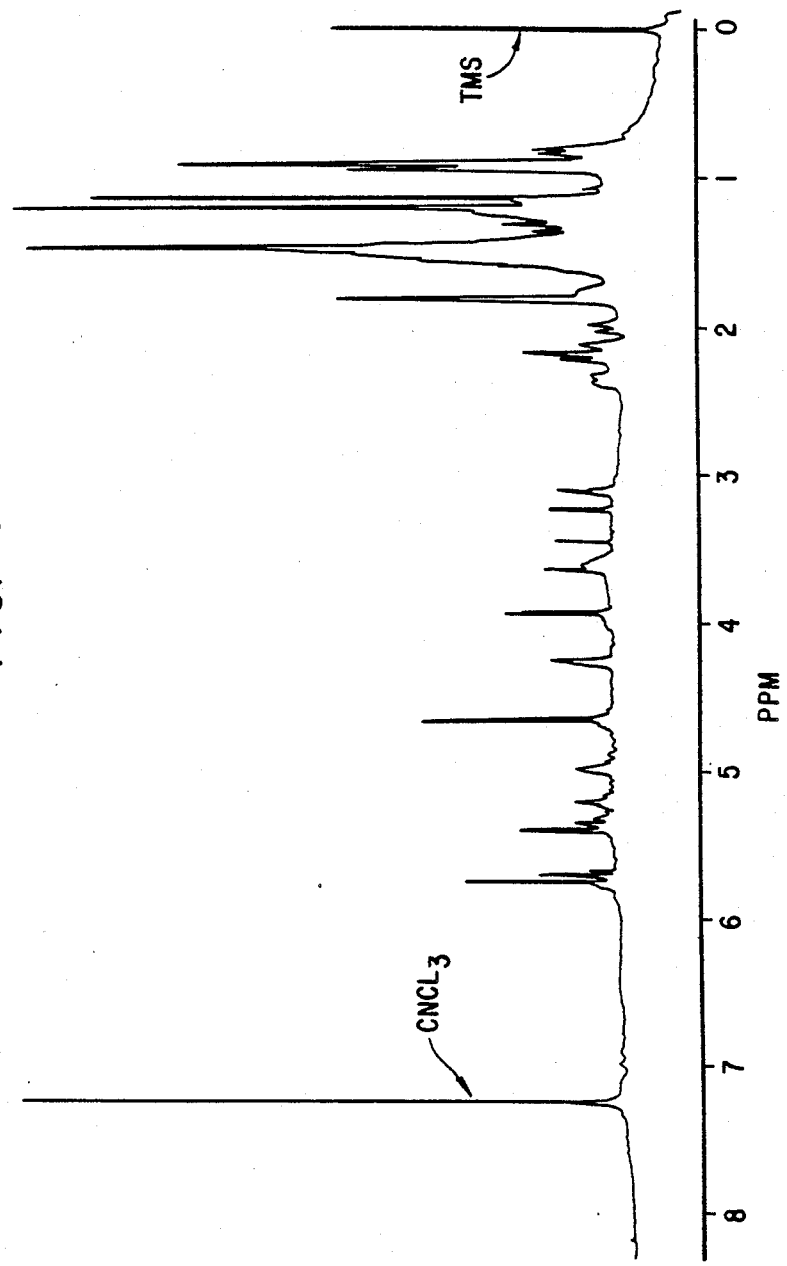
Figure 14:
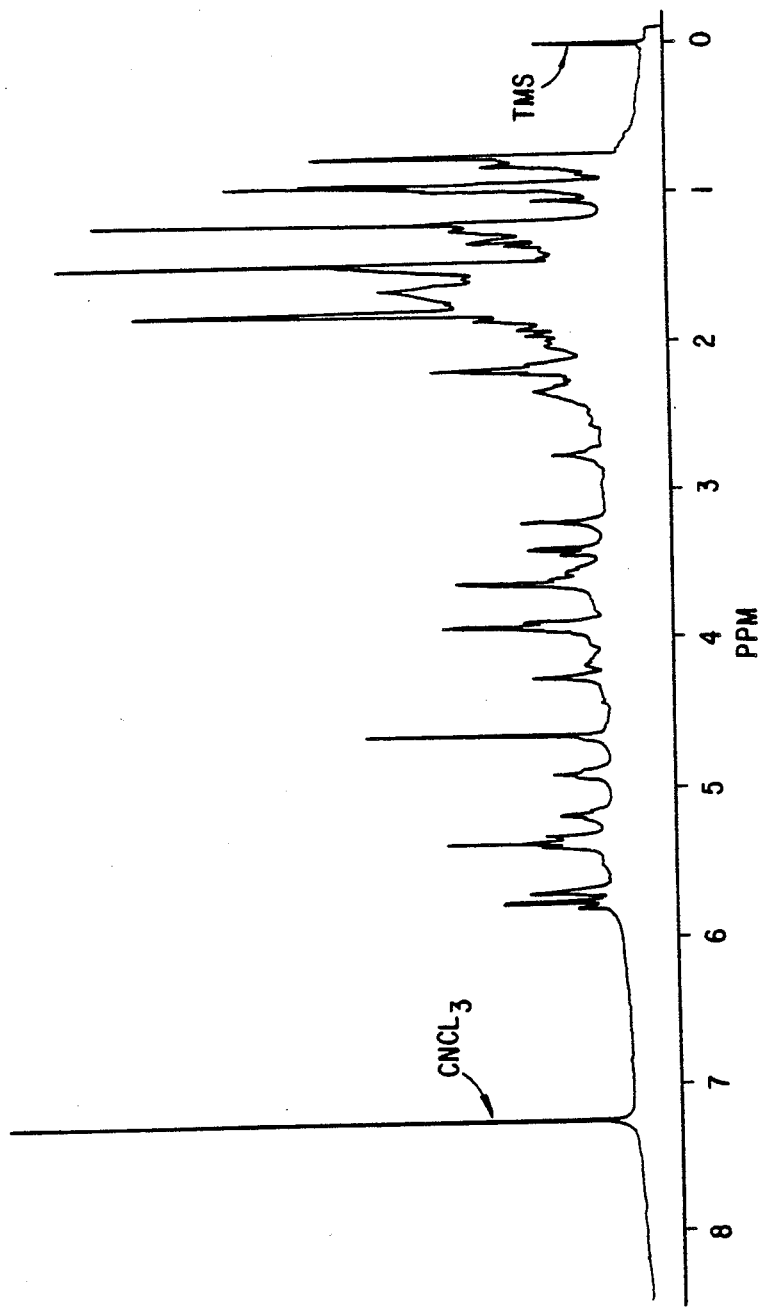
Figure 15:
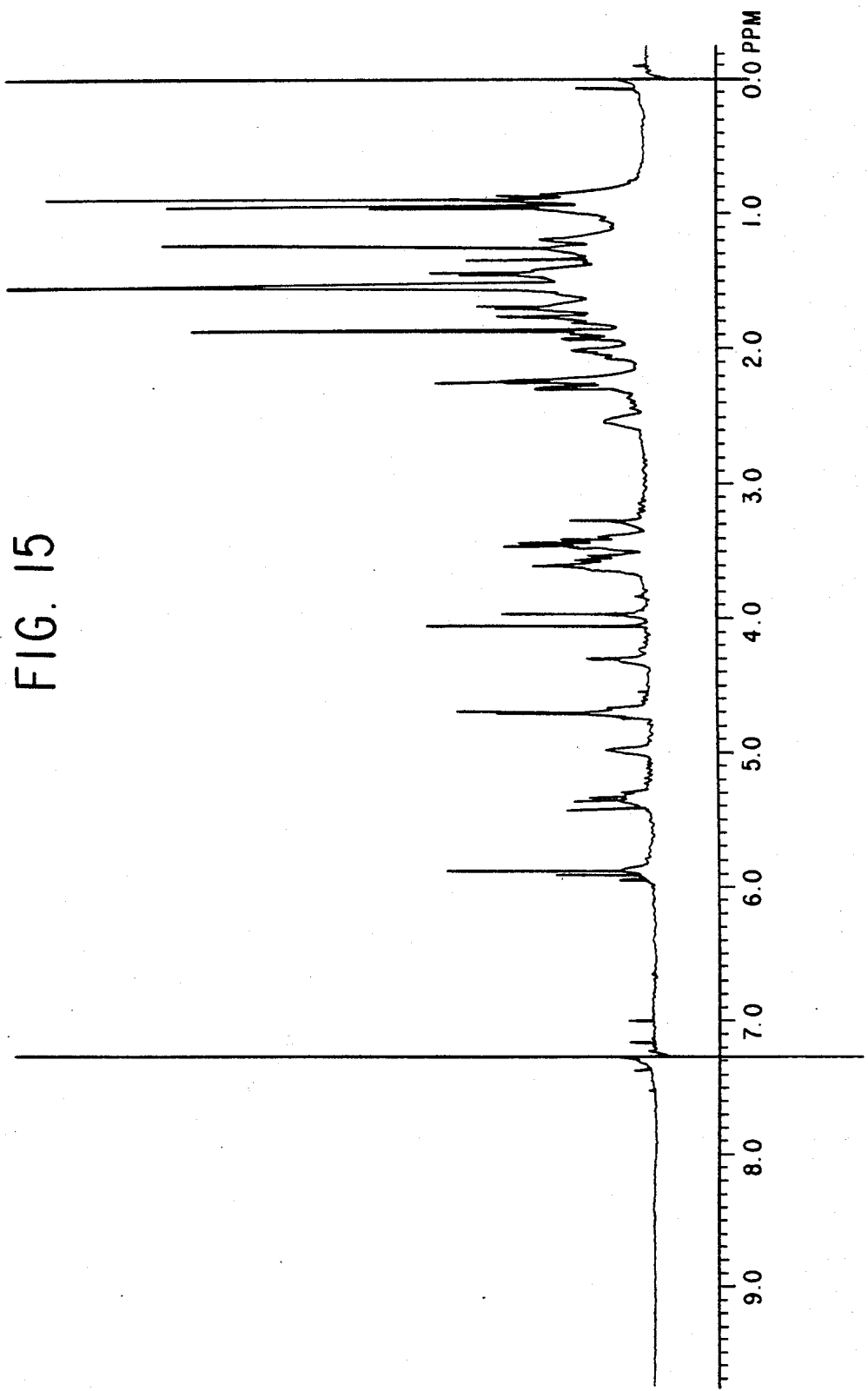
Figure 16:
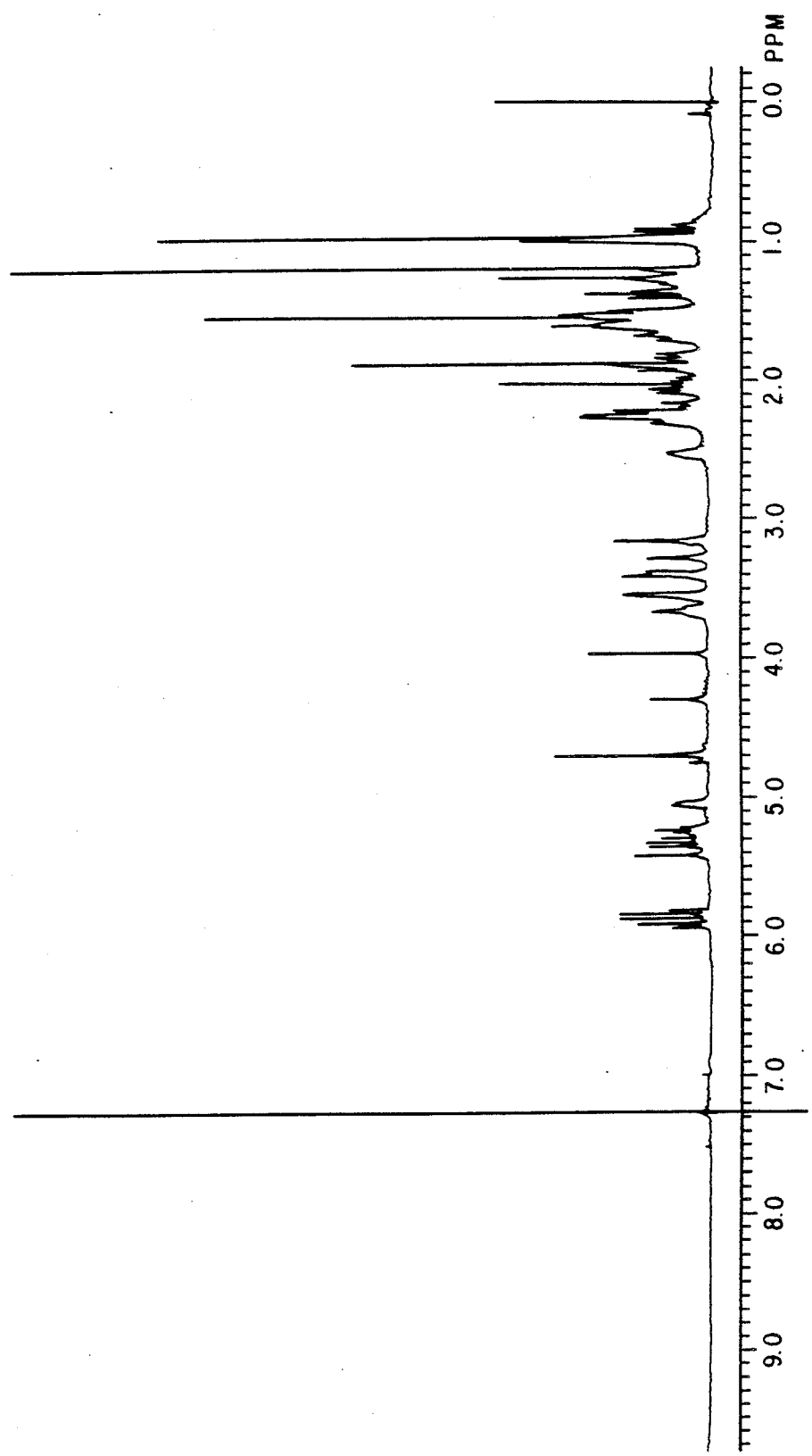
Figure 17:
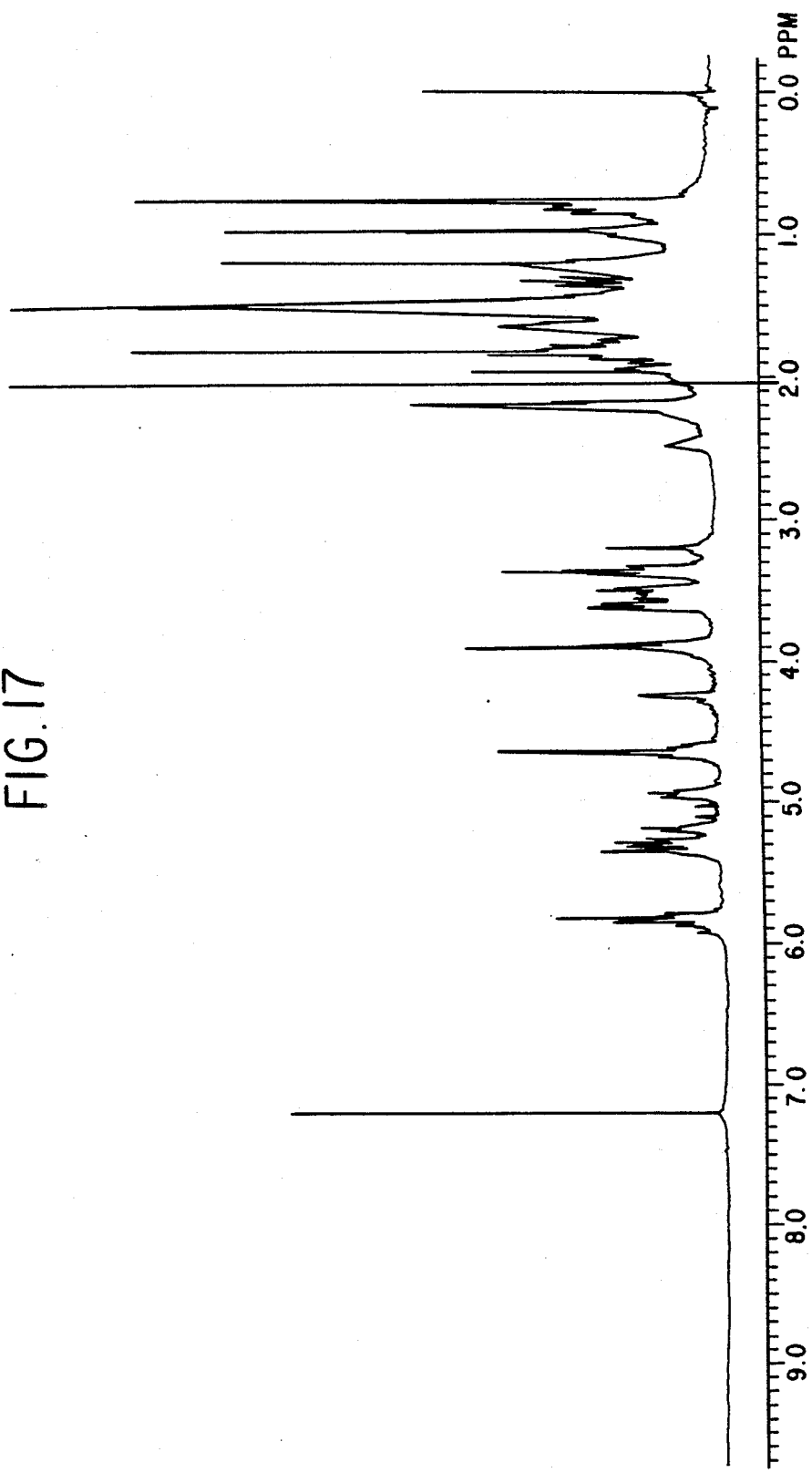
Figure 18:
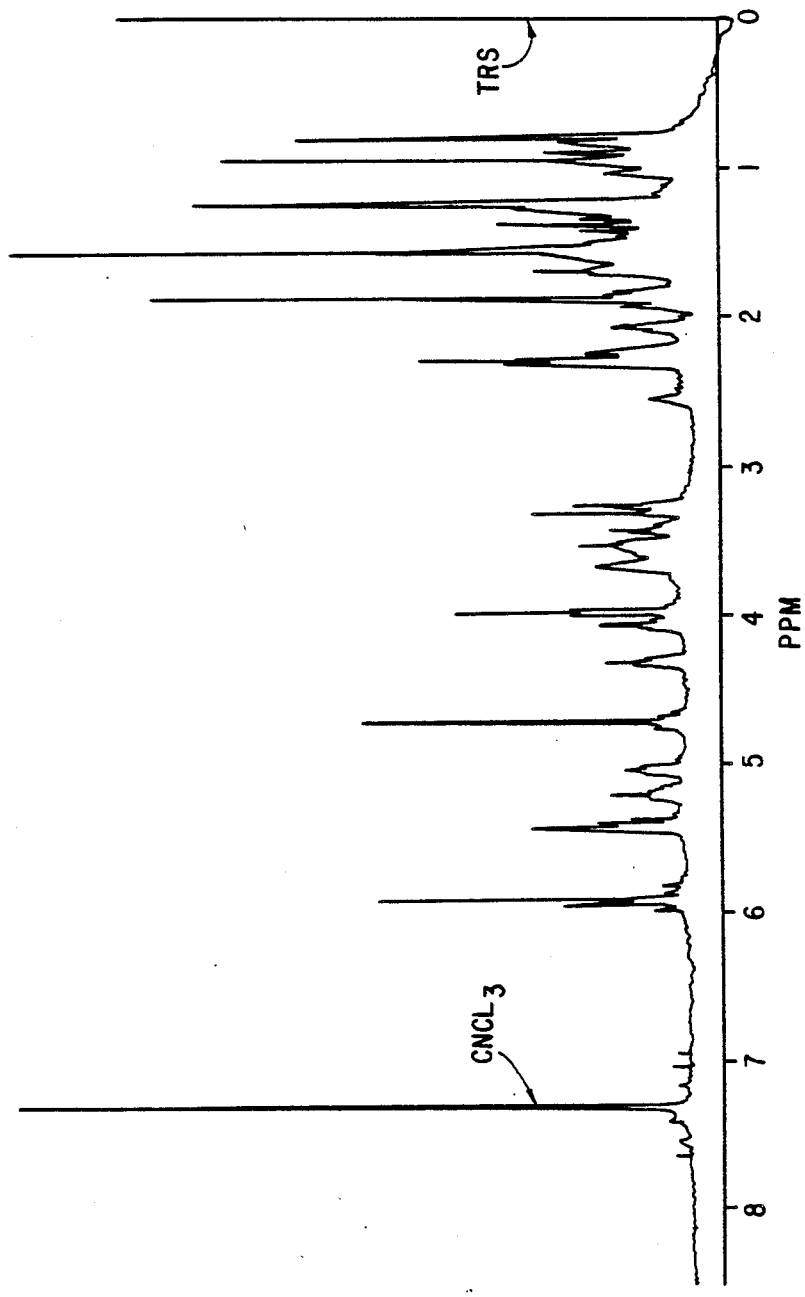

FIGS. 7 to 18 represent the nuclear magnetic resonance spectra for Structures 7 to 18 respectively.

Using 13-deoxy-22,23-dihydro avermectin B1b aglycone as the substrate produced nine hydroxylated products of the following structure:

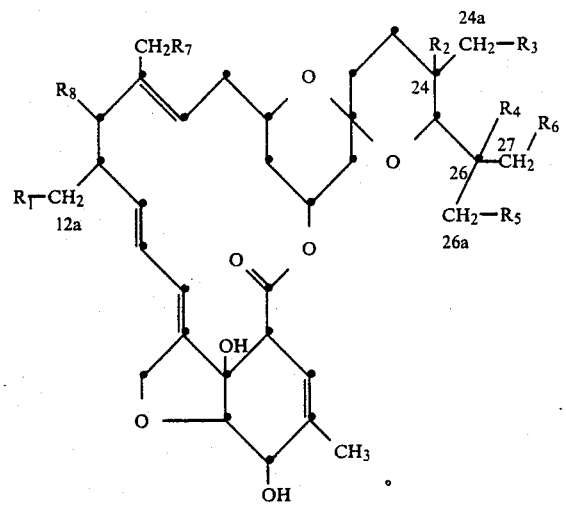

wherein $R_1$, $R_2$, $R_3$, $R_4$, $R_5$, $R_6$, $R_7$ and $R_8$ have the following meanings:

| Structure | Name | $R_1$ | $R_2$ | $R_3$ | $R_4$ | $R_5$ | $R_6$ | $R_7$ | $R_8$ |
|---|---|---|---|---|---|---|---|---|---|
| 19 | 13-epi-12a-dihydroxy-22,23-dihydro avermectin B1b aglycone | OH | H | H | H | H | H | H | OH(epi) |
| 20 | 13-epi-26-dihydroxy-22,23-dihydro avermectin B1b aglycone | H | H | H | OH | H | H | H | OH(epi) |
| 21 | 13-epi-27-dihydroxy-22,23-dihydro avermectin B1b aglycone | H | H | H | H | H | OH | H | OH(epi) |
| 22 | 13-deoxy-12a-hydroxy-22,23-dihydro avermectin B1b aglycone | OH | H | H | H | H | H | H | H |
| 23 | 13-deoxy-26-hydroxy-22,23-dihydro avermectin B1b aglycone | H | H | H | OH | H | H | H | H |
| 24 | 13-deoxy-27-hydroxy-22,23-dihydro avermectin B1b aglycone | H | H | H | H | H | OH | H | H |
| 25 | 13-deoxy-12a,26-dihydroxy-22,23-dihydro avermectin B1b aglycone | OH | H | H | OH | H | H | H | H |
| 26 | 13-deoxy-12a,27-dihydroxy-22,23-dihydro avermectin B1b aglycone | OH | H | H | H | H | OH | H | H |
| 27 | 13-deoxy-14a,26-dihydroxy-22,23-dihydro avermectin B1b aglycone | H | H | H | OH | H | H | OH | H |

High resolution mass spectrometry data for the foregoing nine compounds are as follows:

| Structure | Found | Calcd | For | Assignment |
|---|---|---|---|---|
| 19 | 588.3295 | 588.3298 | $C_{33}H_{48}O_9$ | $M^+$ |

-continued

| Structure | Found | Calcd | For | Assignment |
|---|---|---|---|---|
| 20 | 588.3272 | 588.3298 | $C_{33}H_{48}O_9$ | $M^+$ |
| 21 | 588.3295 | 588.3298 | $C_{33}H_{48}O_9$ | $M^+$ |
| 22 | 572.3343 | 572.3349 | $C_{33}H_{48}O_8$ | $M^+$ |
| 23 | 572.3343 | 572.3349 | $C_{33}H_{48}O_8$ | $M^+$ |
| 24 | 572.3350 | 572.3349 | $C_{33}H_{48}O_8$ | $M^+$ |
| 25 | 588.3283 | 588.3298 | $C_{33}H_{48}O_9$ | $M^+$ |
| 26 | 588.3301 | 588.3298 | $C_{33}H_{48}O_9$ | $M^+$ |
| 27 | 588.3295 | 588.3298 | $C_{33}H_{48}O_9$ | $M^+$ |

Figure 19:
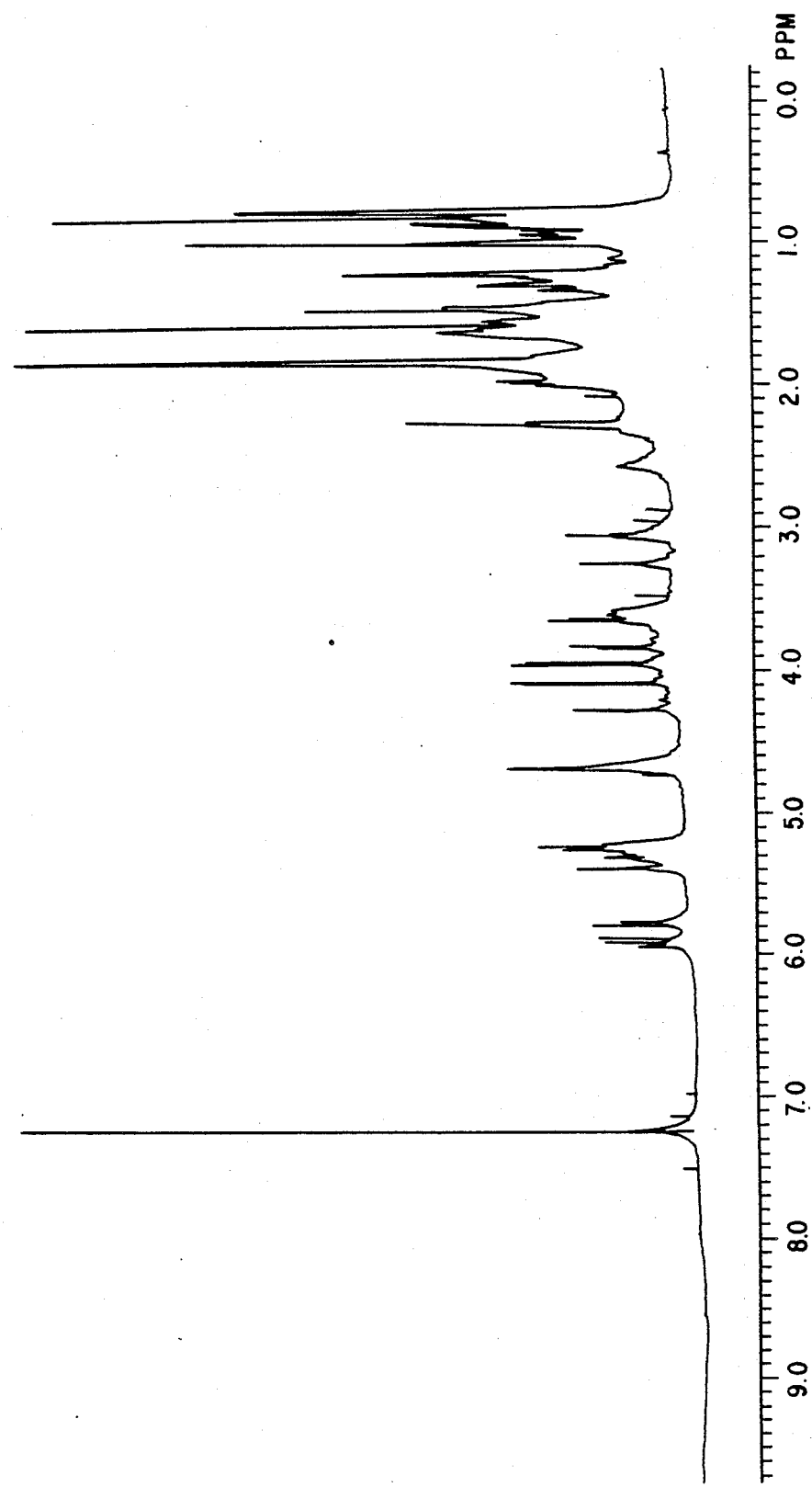
Figure 20:
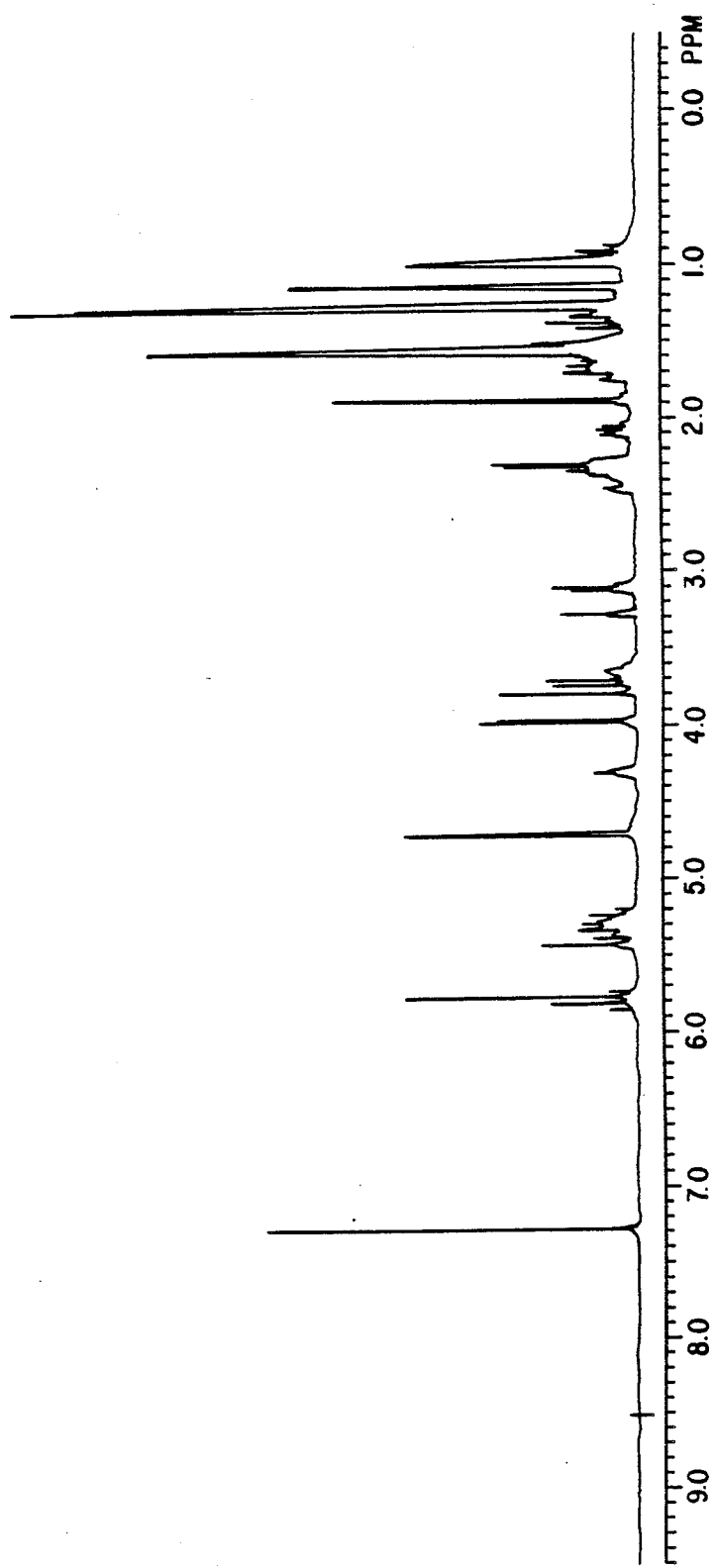
Figure 21:
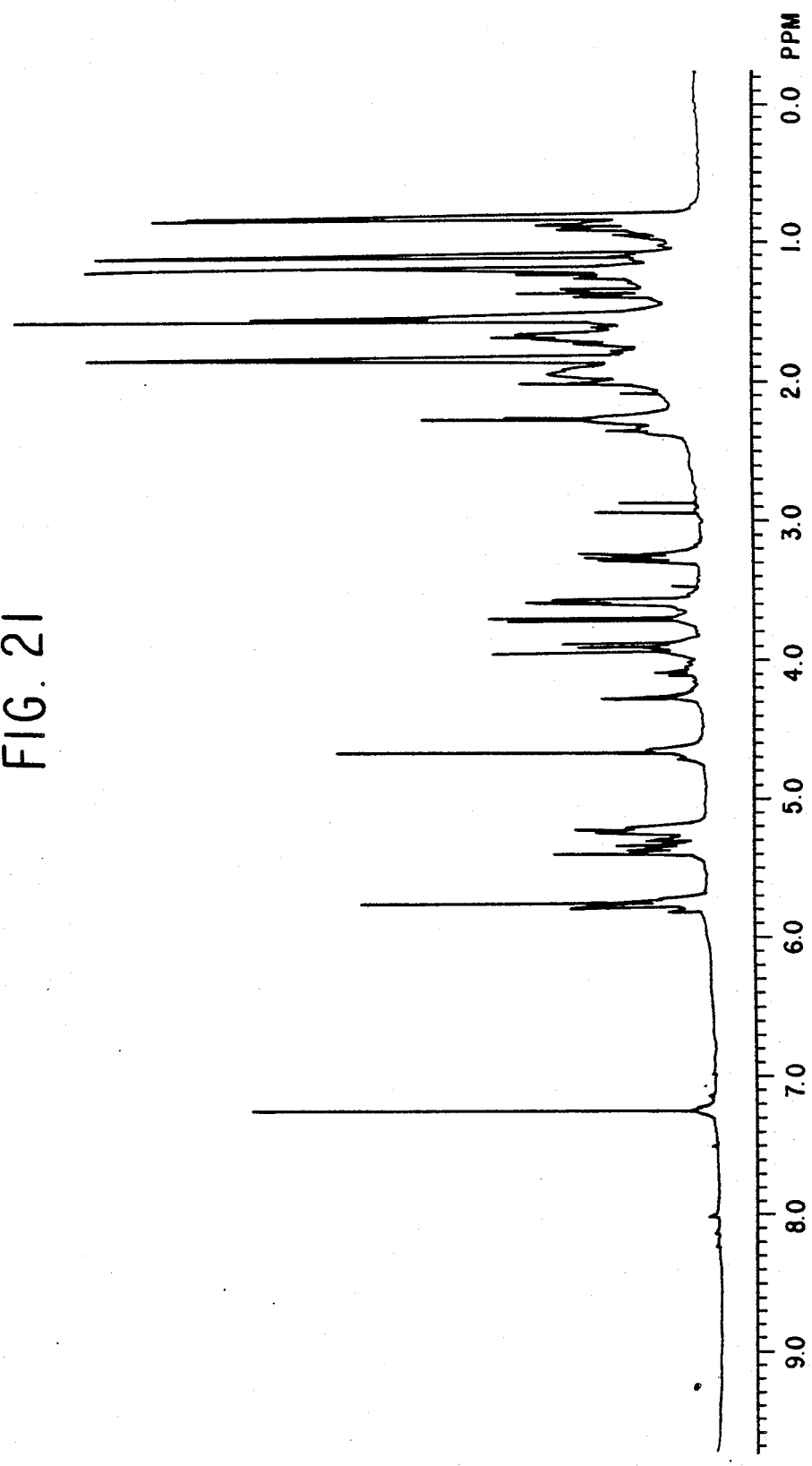
Figure 22:
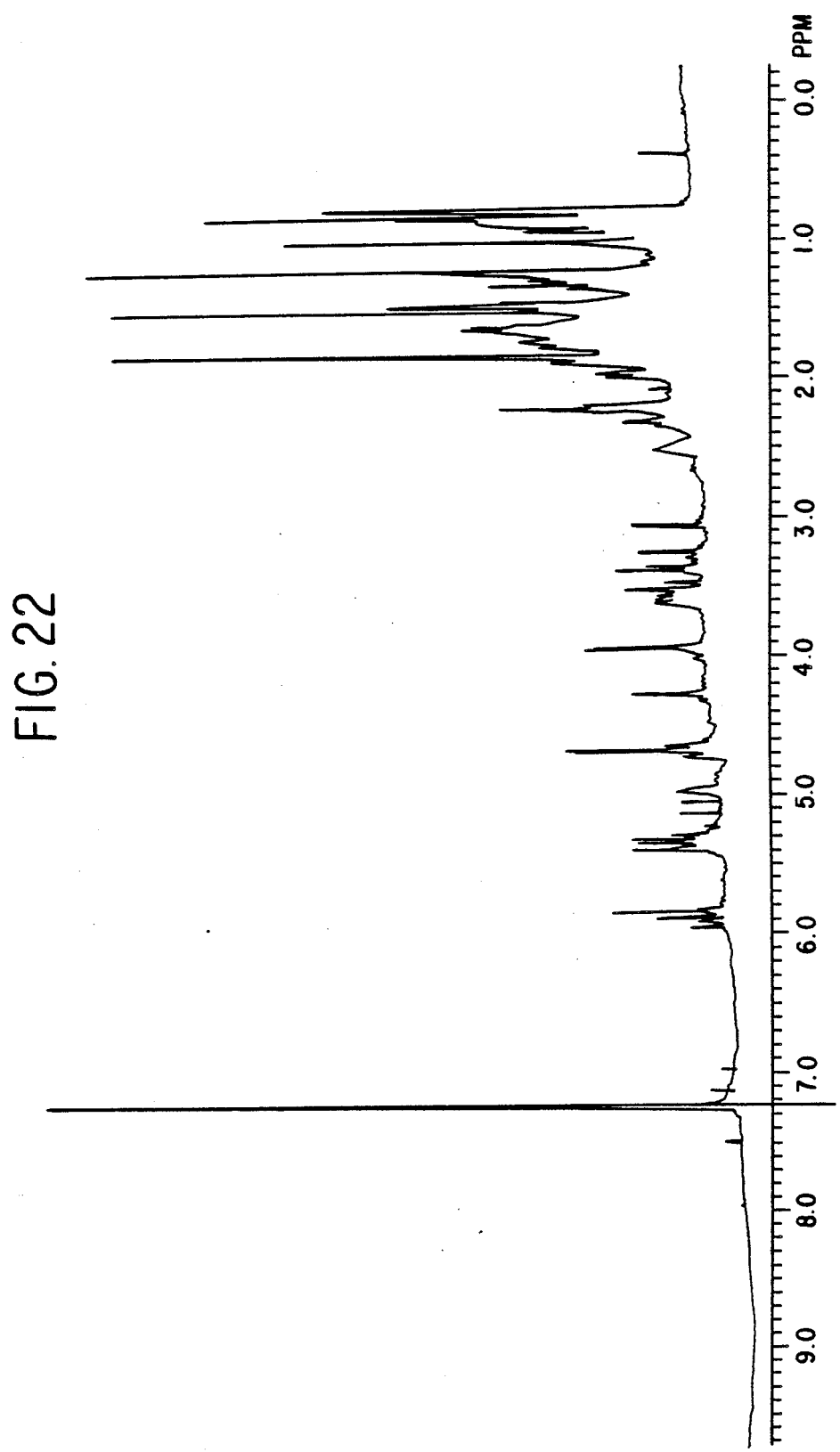
Figure 23:
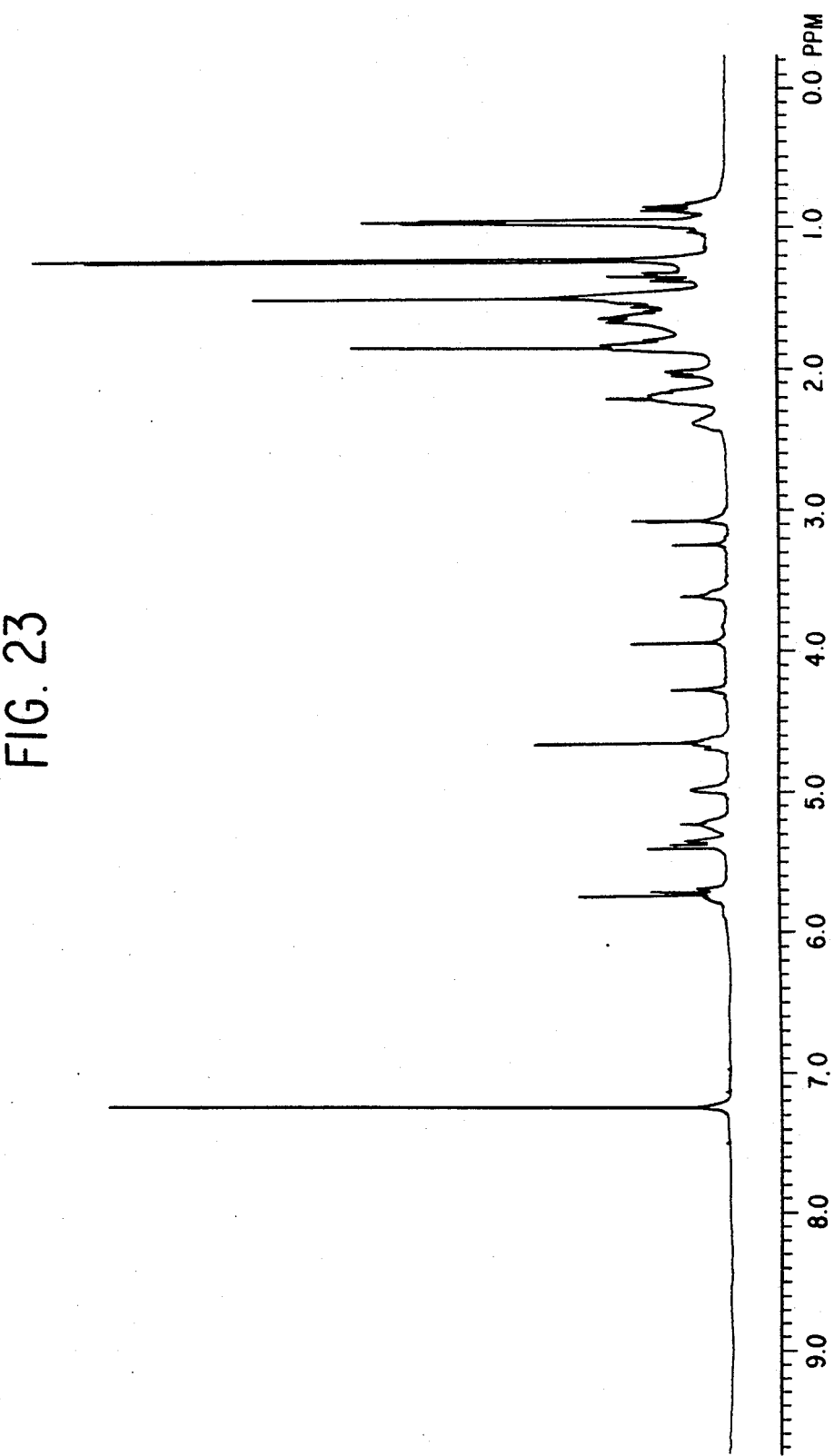
Figure 24:
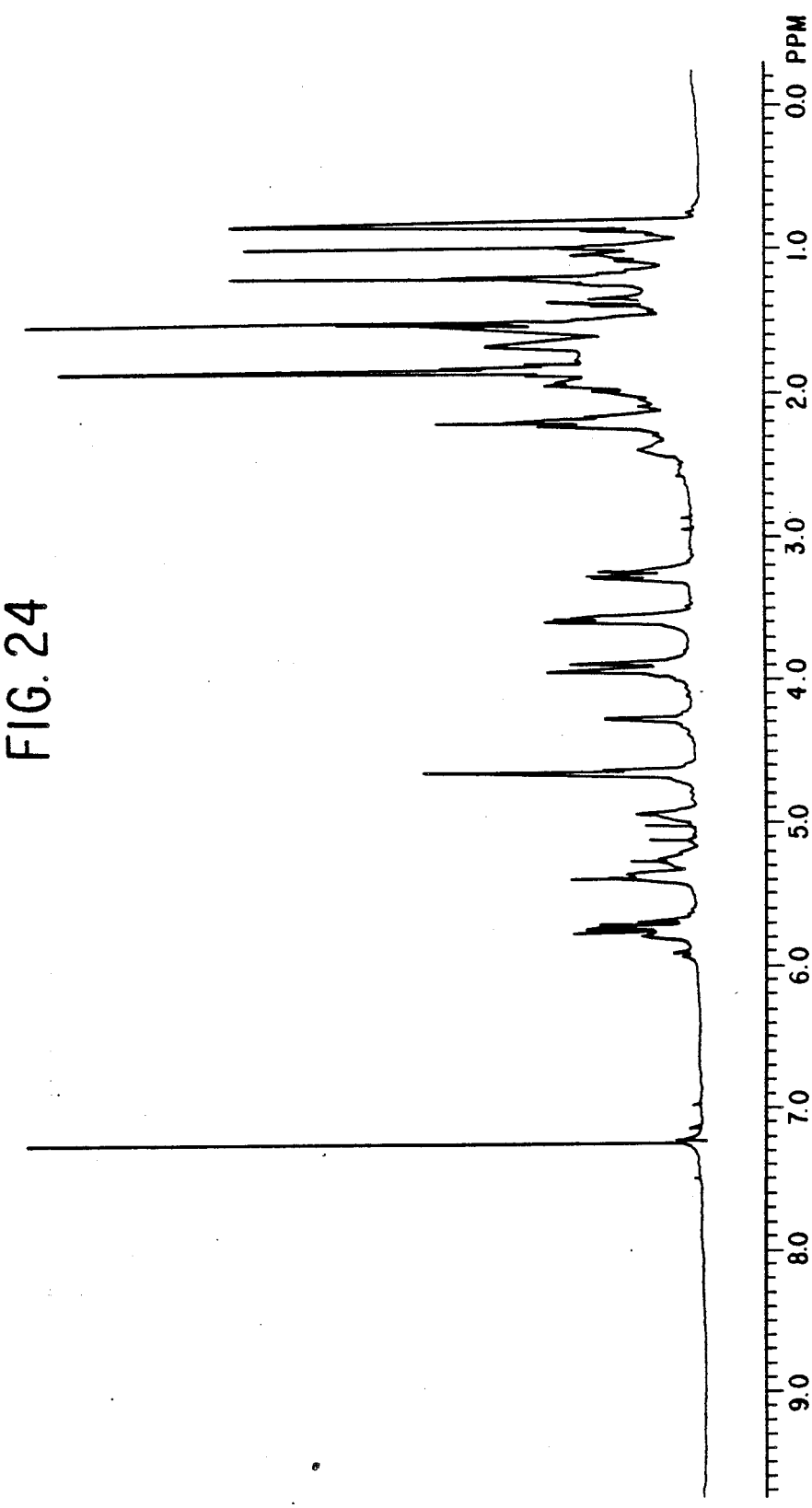
Figure 25:
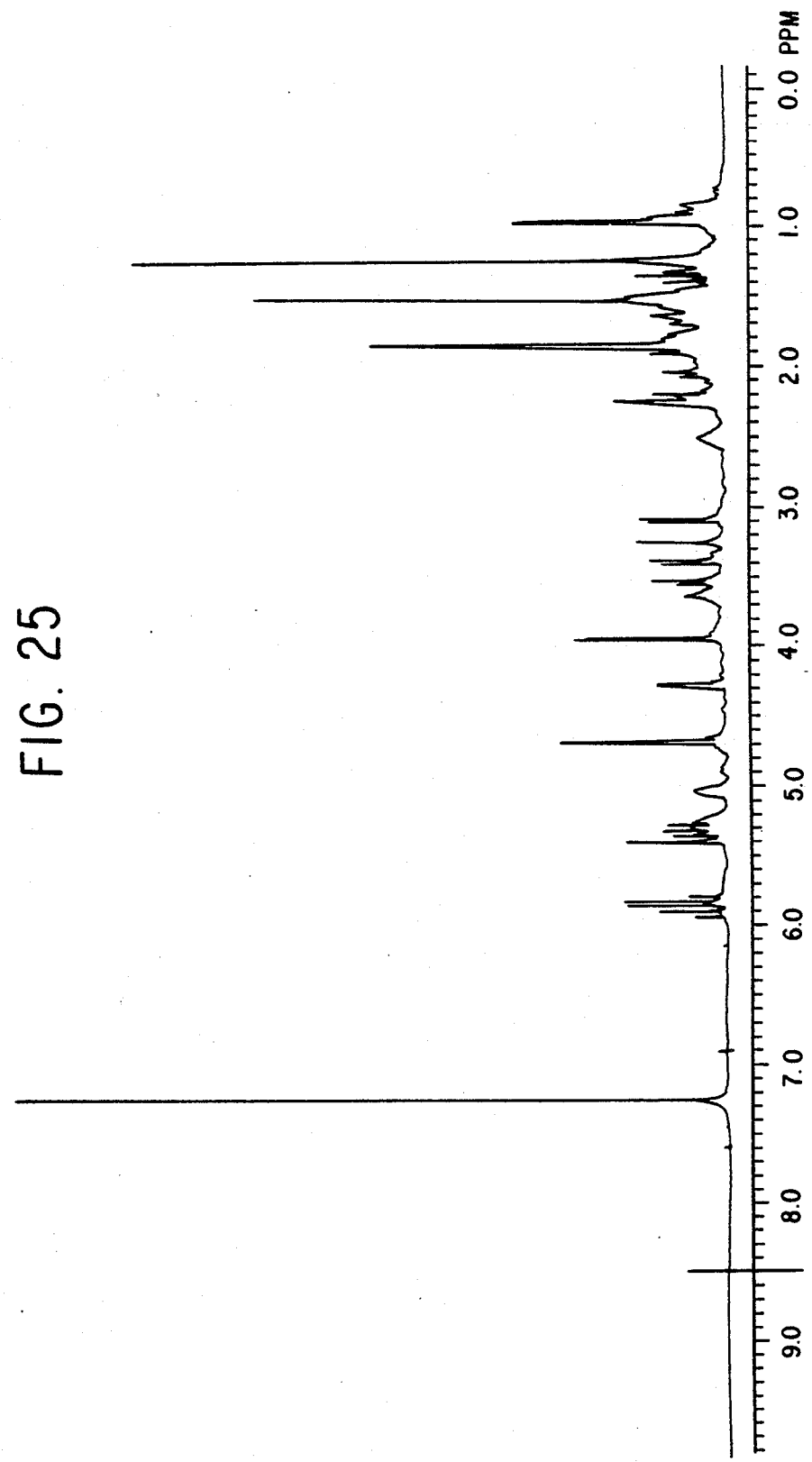
Figure 26:
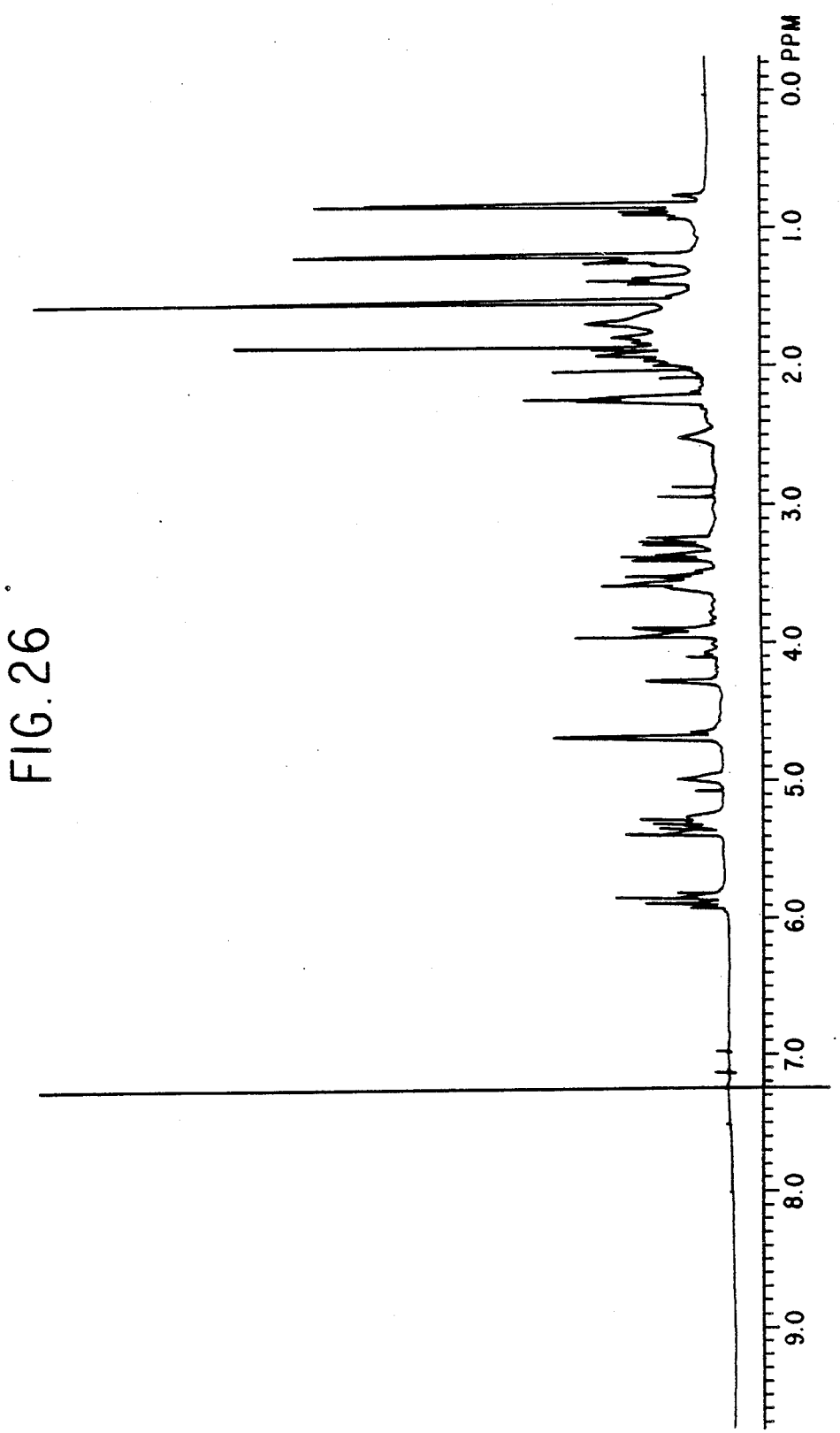
Figure 27:
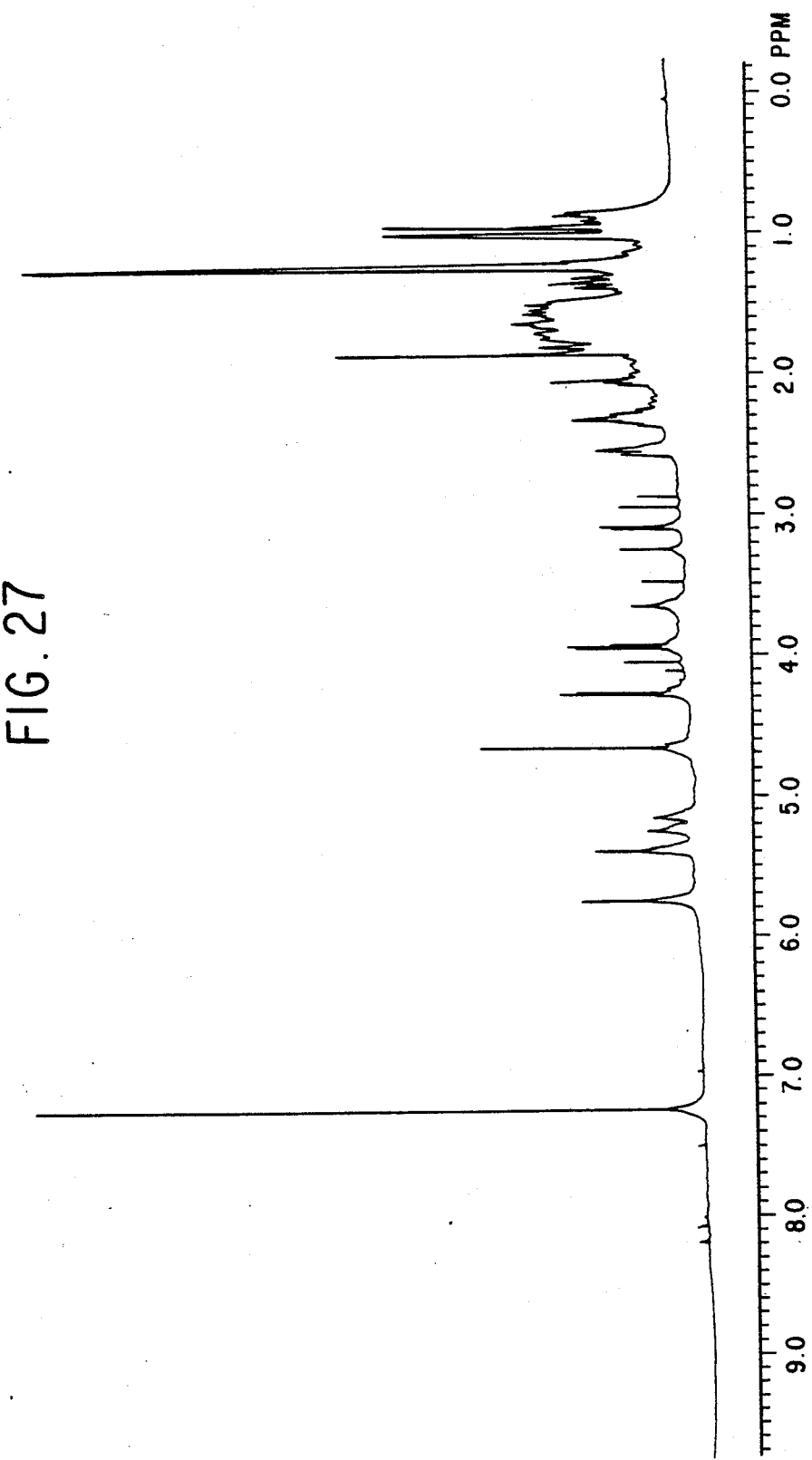

FIGS. 19 to 27 represent the nuclear magnetic resonance spectra for Structures 19 to 27 respectively.

The novel compounds of this invention have significant parasiticidal activity as anthelmintics, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compounds are also useful against parasites which infect humans. The most common genera of parasites of the gastro-intestinal tract of parasites of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp. and the housefly *Musca domestica.*

The compounds are also useful against insect pests of stored grains such as Tribolium sp., Tenebrio sp. and of agricultural plants such as spider mites, (Tetranychus sp.), aphids, (Acyrthiosiphon migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or dicalcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and constant of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol, formal and aqueous parenteral formulations are also used. The active compound or compounds are dissolved or suspended in the parenteral formulation for administration; such formulations generally contain from 0.005 to 5% by weight of the active compound.

Although the antiparasitic agents of this invention find their primary use in the treatment and/or prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally, good results are obtained with our novel compounds by the oral administration of from about 0.001 to 10 mg per kg of animal body weight, such total dose being given at one time or in divided doses over a relatively short period of time such as 1–5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired antiparasitic result.

In using the compounds of this invention, the individual components may be isolated and purified and used in that form. Alternatively, mixtures more of the individual components may be used. It is not necessary to completely separate the various compounds obtained from the purification of the fermentation broth. Generally, there is obtained a mixture containing two or more of the compounds, but having other unrelated compounds excluded therefrom, and such mixture may be used for the prevention and treatment of parasitic diseases as described herein. Such a mixture generally will contain unequal proportions of the compounds, however, all of the compounds have substantial activity and the antiparasitic activity of the mixture can be accurately determined.

In addition, where the compounds are to be added to an animal's feed, it is possible to utilize the dried mycelial cake from the fermentation broth. The mycelia contain a preponderance of the activity and since the level of the activity of the mycelia can be determined, it can be added directly to the animal's feed.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The anthelmintic activity of the instant compounds may be determined by orally administering via the feed, a sample of the individual compound, a mixture of such compounds, a concentrated extract, and the like to a mouse which had been infected 3 days earlier with a gastrointestinal parasite. At 11, 12 and 13 days after the initiation of the medication, the feces of the mouse are examined for eggs, and one the next day the mouse is sacrificed and the number of worms present in the proximal portion of the small intestine are determined. An active compound is observed when there is a significant reduction of egg and worm counts when compared to infected, unmedicated controls.

The following examples are being provided in order that the instant invention may be more fully understood. Such examples are not to be construed as being limitative of the invention.

EXAMPLE 1

Transformation Methodology

| Media: | g/l |
|---|---|
| Seed Medium A | |
| Dextrose | 4.0 g |
| Nutrient Broth | 4.0 g |
| Yeast Extract | 4.0 g |
| Malt Extract | 10.0 g |

| Media: | g/l |
|---|---|
| 1000 ml distilled H$_2$O pH 7.3 q.s. | |
| Slant Medium B | |
| Medium A plus Agar | 20.0 g |
| Transformation Medium C | |
| Same as Medium A, substrate at | 0.25 g |

A lypophile tube of *Cunninghamella blakesleeana* MF-4415, ATCC 8688a was aseptically opened and grown in seed medium A (40 ml in a 250 ml 3-baffle Erlenmeyer flask) for 48 hours on a rotary shaker (220 rpm) at 27° C.

This seed was then used to inoculate slants (medium B) and transformation flasks (medium C).

The substrate was added post sterilization and prior to inoculation. Methanol was used to solubilize the substrate for filter sterilization and addition. The transformation flasks (40 ml medium C in 250 ml 3-baffle Erlenmeyer flask) were incubated for 7 days with agitation (220 rpm) at 27° C. Following incubation, the whole broths were extracted as follows:

Extraction Methodology a. 50 ml methylene chloride was added to 40 ml whole broth and mechanically agitated for 15 minutes. The emulsion was broken by centrifugation. Step a was repeated 3 times.

b. The pooled methylene chloride extracts were taken to dryness under vacuum.

c. The dried methylene chloride fraction was solubilized with 25 ml ($\times$3) ethanol/0.1M K$_2$HPO$_4$, pH 7.0 (40/60). The three extracts were pooled.

d. The phosphate buffer:ethanol fraction was extracted with 25 ml cyclohexane ($\times$3) to remove any residual substrate. The cyclohexane fractions were pooled and taken to dryness under vacuum. The residue was solubilized with a known volume of methanol and dried with anhydrous Na$_2$SO$_4$.

e. The phosphate buffer:ethanol fraction previously extracted with cyclohexane, was then extracted with 25 ml methylene chloride ($\times$3) to separate the altered substrate. The methylene chloride fractions were pooled and taken to dryness under vacuum. The residue was solubilized with a known volume of methanol and dried with anhydrous Na$_2$SO$_4$.

f. All organic fractions were submitted for HPLC analysis to determine and isolate non-substrate avermectins.

Specific Example 1A

Culture: *Cunninghamella blakesleeana* MA-4415, ATCC 8688a
Substrate: 1 mg $^3$H-22,23, dihydro avermectin Bla aglycone
Sample 1: Cyclohexane Ext.
Sample 2: Methylene chloride Ext.

Specific Example 1B

Culture: *Cunninghamella blakesleeana* MA-4415, ATCC 8688a
Substrate: 25 mg, 22,23-dihydro avermectin Bla aglycone. Twenty-five flasks pooled and extracted for product isolation and identification.
Sample 3: Cyclohexane Ext.
Sample 4: Methylene chloride Ext.

Specific Example 1C

Culture: *Cunninghamella blakesleeana* MA-4415, ATCC 8688a
Substrate: 75 mg, 22,23-dihydro avermectin Bla aglycone. Seventy-five flasks pooled and extracted for product isolation and identification.
Sample 5: Cyclohexane Ext.
Sample 6: Methylene chloride Ext.

EXAMPLE 2

Sample 4 of Example 1B, the methylene chloride fraction, was taken up in 700 mcl of 75/25 methanol/water and subjected to preparative chromatography on a DuPont Zorbax ODS reverse phase $C_{18}$ column 2.1×25 cm at room temperature using a solvent system of 75/25 methanol/water at a flow rate of 10 ml/minutes. The effluent stream was monitored at 243 nm using an LDC Spectro-Monitor II with a 1 mm path length cell at a setting of 0.64 AUFS. Twenty-one fractions were collected. Selected fractions were concentrated to dryness.

Fraction number 6 labeled 1
Fraction numbers 12 and 13 combined, labeled 2
Fraction numbers 14 and 15 combined, labeled 3
Fraction numbers 16 and 17 combined, labeled 4

These fractions were quantitated by their ultra-violet absorption at 243 nm using the following method.

$$\text{Conc.} = \frac{\text{O.D. 243 nm} \times 10 \times \text{dilution}}{0.365 \text{ (O.D. 10 mcg/ml avermectin Bla at 243 nm)}} \times \frac{602}{875}$$

The total amount per sample was calculated to be as follows:

Fraction 1 3.770 mg. Compound 3
Fraction 2 1.187 mg. Compound 5
Fraction 3 0.486 mg. Compound 4
Fraction 4 0.916 mg. Compound 6

Structure

Compound 3 24a-hydroxy-22,23-dihydro avermectin Bla aglycone
Compound 5 26a-hydroxy-22,23-dihydro avermectin Bla aglycone
Compound 4 26-hydroxy-22,23-dihydro avermectin Bla aglycone
Compound 6 27-hydroxy-22,23-dihydro avermectin Bla aglycone

EXAMPLE 3

Sample 6 of Example 1C was taken up in 1 ml of 75/25 methanol/water. The solution was filtered to remove insolubles. The clear filtrate was labeled Sample 1. The insolubles were taken up in 1 ml of methanol and labeled Sample 2. HPLC assay of Sample 2 indicated a loss of approximately six percent of each of the desired compounds.

Sample 1 was subjected to preparative chromatography on a DuPont Zorbax ODS reverse phase $C_{18}$ column 2.1×25 cm at room temperature using a solvent system of 75/25 methanol/water at a flow rate of 10 ml/minute. The effluent stream was monitored at 243 nm using an LDC Spectro-Monitor II with a 1 mm path length cell at a settng of 1.28 AUFS. Fifty-two fractions were collected. Selected fractions were concentrated to dryness.

Fraction number 13 was labeled Sample 3 and used in Example 4.

Fraction numbers 45 thru 47 were combined affording Compound 1.

The fractions were quantitated by their ultra-violet absorption at 243 nm using the following method.

$$\text{Conc.} = \frac{\text{O.D. 243 nm} \times 10 \times \text{dilution}}{0.365 \text{ (O.D. 10 mcg/ml avermectin Bla at 243 nm)}} \times \frac{602}{875}$$

The total amount of compound in the sample was calculated to be 0.415 mg of Compound 1 (12a-hydroxy-22,23-dihydro avermectin Bla aglycone).

EXAMPLE 4

Sample 3 of Example 3 was concentrated to dryness and taken up in 200 mcl of 70/30 methanol/water and subjected to preparative HPLC chromatography on a DuPont Zorbax ODS reverse phase $C_{18}$ column 0.94×25 cm at room temperature using a solvent system of 70/30 methanol/water at a flow rate of 2 ml/minute. The effluent stream was monitored at 243 nm using an LDC Spectro-Monitor II with a 1 mm path length cell at a setting of 0.64 AUFS. Eleven fractions were collected. Fraction number 10 was concentrated to dryness. The fraction was quantitated by the ultra-violet absorption specified in Example 3 and contained 0.244 mg of Compound 2 (24-hydroxy-22,23-dihydro avermectin Bla aglycone).

Specific Example 5A

Culture: *Cunninghamella blakesleeana* MA-4415, ATCC-8688a
Substrate: 2 mg 13-deoxy-22,23-dihydro avermectin Bla aglycone
Sample 7: Cyclohexane Ext.
Sample 8: Methylene chloride Ext.

Specific Example 5B

Culture: *C. blakesleeana* MA-4415, ATCC-8688a
Substrate: 50 mg 13-deoxy-22,23-dihydro avermectin Bla aglycone. Fifty flasks pooled for product isolation and identification.
Sample 9: Cyclohexane Ext.
Sample 10: Methylene chloride Ext.

EXAMPLE 6

The cyclohexane extract, Specific Example 5B, sample 9, was concentrated to dryness and the residue taken up in 1 ml of methylene chloride and chromatographed on a dry packed E. Merck silica gel 60 (0.04 to 0.063 mm particle size) column of approximately 1 ml in volume. The chromatography was carried out using a stepwise gradient as follows: (1) 3 ml methylene chloride, (2) 5 ml 90/10 v/v methylene chloride/ethyl acetate, (3) 5 ml 50/50 v/v methylene chloride/ethyl acetate, and (4) 5 ml 50/50 v/v methylene chloride/methanol. Twenty fractions of approximately 1 ml each were collected. Aliquots of the fractions were analyzed by reverse phase $C_{18}$ HPLC chromatography on a DuPont Zorbax ODS column (4.6 mm×25 cm) at room temperature. A solvent system of 85/15 v/v methanol/water at a flow rate of 1 ml/minute was used and the effluent monitored at 243 nm 0.1 AUFS using an L.D.C. Spectro-Monitor III. Fractions 10 thru 17 contained the compounds of interest with HPLC retention times of 12.6 to 18.2 minutes. Fractions 10 thru 17 were combined and concentrated to dryness. The residue was labeled A.

EXAMPLE 7

The residue A from Example 6 was taken up in 500 mcl of 75/25 v/v methanol/water and filtered. The filtrate was subjected to preparative HPLC chromatography on a DuPont Zorbax ODS $C_{18}$ column 0.94×25 cm at room temperature. The chromatography was carried out using the following gradient generated by a DuPont 8800 Gradient Controller, at a flow rate of 4 ml/minute.

Gradient: 75/25 methanol/water for 75 minutes then a linear gradient to 85/15 methanol/water over five minutes, hold at 85/15 for 20 minutes then a linear gradient to 100% methanol over five minutes, hold at 100% methanol for 15 minutes. The effluent stream was monitored at 243 nm, 0.32 AUFS using an L.D.C. Spectro-Monitor II with a 1 mm path length cell. Eleven fractions were collected based on the ultra-violet trace. Fractions 7 and 10 were each concentrated to dryness. The residue from fraction No. 7 was taken up in 5 ml of methanol and labeled B. The residue from fraction No. 10 was also taken up in 5 ml of methanol and labeled C. An ultra-violet absorbance assay was performed on each sample and the following calculation used to determine total concentration of sample.

$$\text{Total concentration} = \frac{\text{O.D. at 243 nm} \times 10 \times \text{dilution}}{0.365} \times \frac{571}{875} \times \text{sample volume}$$

| Sample | Total Conc. | Structure | Identity |
|---|---|---|---|
| A | 159 mcg | 13 | 13-deoxy-26-hydroxy-22,23-dihydro avermectin B1a aglycone |
| C | 314 mcg | 14 | 13-deoxy-26a-hydroxy-22,23-dihydro avermectin B1a aglycone |

EXAMPLE 8

The methylene chloride extract, Specific Example 5B, sample 10, was concentrated to dryness and the residue taken up in 1 ml of 75/25 v/v methanol/water and subjected to preparative HPLC chromatography on a DuPont Zorbax ODS $C_{18}$ column 2.1×25 cm at room temperature. The chromatography was carried out using the following gradient generated by a DuPont 8800 Gradient Controller at a flow rate of 10 ml/minute.

Gradient: 75/25 methanol/water for 69 minutes, then a linear gradient to 85/15 methanol/water over 5 minutes, hold at 85/15 for 20 minutes, then a linear gradient to 100% methanol over 5 minutes, hold at 100% methanol for 21 minutes. The effluent stream was monitored at 243 nm 0.32 AUFS using an L.D.C. Spectro-Monitor II with a 1 mm path length cell. Sixty-five fractions were collected based on the ultra-violet trace. The following fractions were selected:

Fractions 4, 5, 6 and 10 combined and labeled D
Fraction 19 labeled E
Fraction 22 labeled F
Fraction 29 labeled G
Fraction 30 labeled H
Fractions 37 and 38 combined and labeled I
Fractions 42 and 43 combined and labeled J
Fraction 62 labeled K Total concentration of samples I, J and K were calculated as in Example 7.

| Sample | Total Conc. | Structure | Identity |
|---|---|---|---|
| I | 503 mcg | 7 | 13-epi,12a-dihydroxy-22,23-dihydro avermectin B1a aglycone |
| J | 960 mcg | 18 | 13-deoxy-12a,27-dihydroxy-22,23-dihydro avermectin B1a aglycone |
| K | 1,045 mcg | 12 | 13-deoxy-12a-hydroxy-22,23-dihydro avermectin B1a aglycone |

EXAMPLE 9

Sample D from Example 8 was concentrated to dryness. The residue was taken up in 200 mcl of methanol and subjected to preparative HPLC chromatography on a DuPont Zorbax ODS $C_{18}$ 0.94×25 cm column at room temperature. The chromatography was carried out using an isocratic solvent system of 65/35 v/v methanol/water at a flow rate of 2 ml/minute. The effluent stream was monitored at 243 nm 0.64 AUFS using an L.D.C. Spectro-Monitor II with a 1 mm path length cell. Eighteen fractions were collected based on the ultra-violet trace. The following fractions were selected. Fractions 9 and 10 were combined and labeled sample L. Fractions 15 and 16 were combined and labeled M. The total concentrations of samples L and M were calculated as in Example 7.

| Sample | Total Conc. | Structure | Identity |
|---|---|---|---|
| L | 350 mcg | 9 | 13-epi,24a-dihydroxy-22,23-dihydro avermectin B1a aglycone |
| M | 222 mcg | 15 | 13-deoxy-12a,24a-dihydroxy-22,23-dihydro avermectin B1a aglycone |

EXAMPLE 10

Sample E from Example 8 was concentrated to dryness. The residue was taken up in 200 mcl of methanol and subjected to preparative HPLC chromatography on a DuPont Zorbax ODS $C_{18}$ column 0.94×25 cm at room temperature. The chromatography was carried out using an isocratic solvent system of 75/25 v/v methanol/water at a flow rate of 4 ml/minute. The effluent stream was monitored at 243 nm 0.64 AUFS using an L.D.C. Spectro-Monitor II with a 1 mm path length cell. Fourteen fractions were collected based on the ultra-violet trace. Fraction 6 was selected and labeled N. The total concentration of this sample was calculated as in Example 7.

| Sample | Total Conc. | Structure | Identity |
|---|---|---|---|
| N | 1,092 mcg | 10 | 13-epi,26-dihydroxy-22,23-dihydro avermectin B1a aglycone |

EXAMPLE 11

Sample F from Example 8 was concentrated to dryness. The residue was taken up in 200 mcl of methanol and subjected to preparative HPLC chromatography on a DuPont Zorbax ODS $C_{18}$ column 0.94×25 cm at room temperature. The chromatography was carried out using an isocratic solvent system of 75/25 v/v methanol/water at a flow rate of 4 ml/minute. The effluent stream was monitored at 243 nm 0.64 AUFS using an L.D.C. Spectro-Monitor II with a 1 mm path length cell. Eleven fractions were collected based on the ultra-violet trace. Fraction No. 6 was selected and labeled sample O. The total concentration of this sample was calculated as in Example 7.

| Sample | Total Conc. | Structure | Identity |
|---|---|---|---|
| O | 640 mcg | 11 | 13-epi,27-dihydroxy-22,23-dihydro avermectin B1a aglycone |

EXAMPLE 12

Sample G from Example 3 was concentrated to dryness. The residue was taken up in 200 mcl of methanol and subjected to preparative HPLC chromatography on a DuPont Zorbax ODS $C_{18}$ column 0.94×25 cm at room temperature. The chromatography was carried out using an isocratic solvent system of 20/45/35 v/v/v acetonitrile/methanol/water at a flow rate of 4 ml/minute. The effluent stream was monitored at 243 nm 0.64 AUFS using an L.D.C. Spectro-Monitor II with a 1 mm path length cell. Fourteen fractions were collected based on the ultra-violet trace. Fraction 7 was labeled sample P. Fractions 9 and 10 were combined and labeled sample Q. The total concentration of sample P was calculated as in Example 7.

| Sample | Total Conc. | Structure | Identity |
|---|---|---|---|
| P | 132 mcg | 8 | 13-epi,14a-dihydroxy-22,23-dihydro avermectin B1a aglycone |

EXAMPLE 13

Sample H from Example 8 was concentrated to dryness. The residue was taken up in 100 mcl of methanol and subjected to preparative HPLC on a DuPont Zorbax ODS $C_{18}$ column 0.94×25 cm at room temperature. The chromatography was carried out using an isocratic solvent system of 20/45/35 v/v/v acetonitrile/methanol/water at a flow rate of 4 ml/minute. The effluent stream was monitored at 243 nm 0.32 AUFS using an L.D.C. Spectro-Monitor II with a 1 mm path length cell. Nine fractions were collected based on the ultra-violet trace. Fraction 9 was combined with sample Q from Example 12 and labeled sample R. Fraction 10 was labeled sample S. The total concentrations of samples R and S were calculated as in Example 7.

| Sample | Total Conc. | Structure | Identity |
|---|---|---|---|
| R | 250 mcg | 16 | 13-deoxy-12a,26-dihydroxy-22,23-dihydro avermectin B1a aglycone |
| S | 985 mcg | 17 | 13-deoxy-12a,26a-dihydroxy-22,23-dihydro avermectin B1a aglycone |

Specific Example 14A

Culture: *Cunninghamella blakesleeana* MA-4415, ATCC 8688a
Substrate: 2 mg 13-deoxy-22,23-dihydro avermectin B1b aglycone
Sample 11: Cyclohexane Ext.
Sample 12: Methylene chloride Ext.

Specific Example 14B

Culture: *C. blakesleeana* MA-4415, ATCC 8688a
Substrate: 50 mg 13-deoxy-22,23-dihydro avermectin B1b aglycone. Fifty flasks pooled for product isolation and identification.
Sample 13: Cyclohexane Ext.
Sample 14: Methylene chloride Ext.

EXAMPLE 15

The methylene chloride extract, Specific Example 14B, sample 14, was concentrated to dryness and the residue taken up in 600 mcl of 70/30 v/v methanol/water and filtered. The filtrate was then subjected to preparative HPLC chromatography on a DuPont Zorbax ODS $C_{18}$ column 0.94×25 cm at room temperature. The chromatography was carried out using the following gradient generated by a DuPont 8800 Gradient Controller, at a flow rate of 4 ml/minute.

Gradient: 70/30 methanol/water for 30 minutes then a linear gradient to 85/15 methanol/water over five minutes, hold at 85/15 for 30 minutes, then linear gradient to 100% methanol over five minutes, hold at 100% methanol for 22 minutes. The effluent was monitored at 243 nm 0.64 AUFS using an L.D.C. Spectro-Monitor II equipped with a 1 mm length cell. Forty-four samples were collected based on the ultra-violet trace. The concentrations of compounds were determined by analytical HPLC comparing area counts of unknown to the area counts/mcg of avermectin B2a aglycone as follows:

$$\text{Concentration of } X = \frac{\text{area counts of } X}{\text{area counts/mcg of avermectin } B2a \text{ aglycone}} \times \frac{573}{588}$$

The following fractions were selected:

Fraction No. 13 labeled sample A
Fraction No. 14 labeled sample B
Fraction No. 18 labeled sample C
Fraction No. 26 labeled sample D
Fraction No. 27 labeled sample E
Fraction No. 29 labeled sample F
Fraction No. 40 labeled sample G

| Sample | Total Conc. | Structure | Identity |
|---|---|---|---|
| A | 364 mcg | 27 | 13-deoxy-14a,26-dihydroxy-22,23-dihydro avermectin B1b aglycone |
| B | 782 mcg | 21 | 13-epi,27-dihydroxy-22,23-dihydro avermectin B1b aglycone |
| C | 2,639 mcg | 20 | 13-epi,26-dihydroxy-22,23-dihydro avermectin B1b aglycone |
| D | 439 mcg | 26 | 13-deoxy-12a,27-dihydroxy-22,23-dihydro avermectin B1b aglycone |
| E | 1,057 mcg | 25 | 13-deoxy-12a,26-dihydroxy-22,23-dihydro avermectin B1b aglycone |
| F | 361 mcg | 19 | 13-epi,12a-dihydroxy-22,23-dihydro avermectin B1b aglycone |
| G | 145 mcg | 22 | 13-deoxy-12a-hydroxy-22,23-dihydro avermectin B1b aglycone |

EXAMPLE 16

The cyclohexane extract, Specific Example 14B, sample 13, was concentrated to dryness. One ml of 70/30 v/v methanol/water was added to the residue and sonicated for 10 minutes, then filtered. The filtrate was labeled H. The insoluble material was taken up in a 1 ml methylene chloride filter wash and concentrated to dryness. One ml of 70/30 v/v methanol/water was added to the residue and sonicated for 10 minutes, then filtered. The filtrate was labeled I. Samples H and I were combined, concentrated to dryness. The residue was taken up in 600 mcl of 85/15 v/v methanol water and subjected to preparative HPLC chromatography on a DuPont Zorbax ODS $C_{18}$ 0.94×25 cm column at room temperature. The chromatography was carried out using the following gradient generated by a DuPont 8800 Gradient controller, at a flow rate of 4 ml/minute.

Gradient: 70/30 methanol/water for 30 minutes then a linear gradient to 85/15 methanol/water over 5 minutes, hold at 85/15 for 30 minutes then linear gradient over 5 minutes to 100% methanol, hold at 100% methanol for 30 minutes.

The effluent stream was monitored at 243 nm 0.32 AUFS using an L.D.C. Spectro-Monitor II equipped with a 1 mm path length cell. Thirty-eight fractions were collected based on the ultra-violet trace. The sample concentrations were calculated as in Example 15. The following fractions were selected:

Fraction No. 27 labeled J
Fraction No. 30 labeled K

| Sample | Total Conc. | Structure | Identity |
|---|---|---|---|
| J | 275 mcg | 23 | 13-deoxy-26-hydroxy-22,23-dihydro avermectin B1b aglycone |
| K | 468 mcg | 24 | 13-deoxy-27-hydroxy-22,23-dihydro avermectin B1b aglycone |

What is claimed is:
1. A compound having the formula:

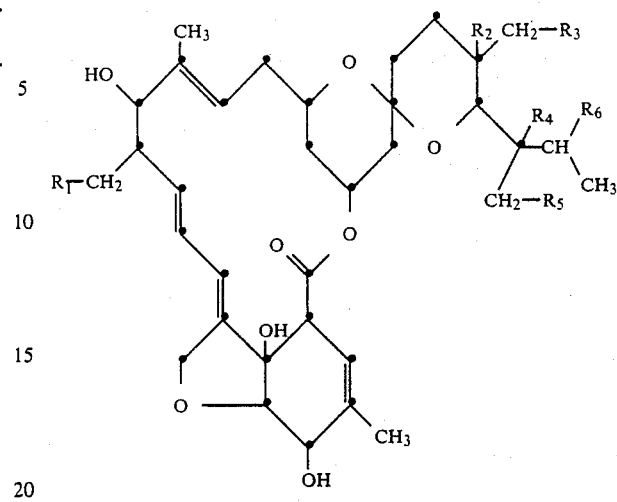

wherein $R_1$, $R_2$, $R_3$, $R_4$, $R_5$ and $R_6$ each may be hydrogen or hydroxy such that one and only one of $R_1$, $R_2$, $R_3$, $R_4$, $R_5$ and $R_6$ is hydroxy at any one time.

2. The compound of claim 1 wherein $R_1$ is hydroxy and $R_2$, $R_3$, $R_4$, $R_5$ and $R_6$ are hydrogen.

3. The compound of claim 1 wherein $R_2$ is hydroxy and $R_1$, $R_3$, $R_4$, $R_5$ and $R_6$ are hydrogen.

4. The compound of claim 1 wherein $R_3$ is hydroxy and $R_1$, $R_2$, $R_4$, $R_5$ and $R_6$ are hydrogen.

5. The compound of claim 1 wherein $R_4$ is hydroxy and $R_1$, $R_2$, $R_3$, $R_5$ and $R_6$ are hydrogen.

6. The compound of claim 1 wherein $R_5$ is hydroxy and $R_1$, $R_2$, $R_3$, $R_4$ and $R_6$ are hydrogen.

7. The compound of claim 1 wherein $R_6$ is hydroxy and $R_1$, $R_2$, $R_3$, $R_4$ and $R_5$ are hydrogen.

8. A method for the treatment of insect, acarid and helminth infections in animals which comprises administering to an animal infected with parasites an effective amount of a compound of claim 1.

9. A composition useful for the treatment of insect, acarid and helminth infections in animals which comprises an inert carrier and an effective amount of a compound of claim 1.

10. A compound having the formula:

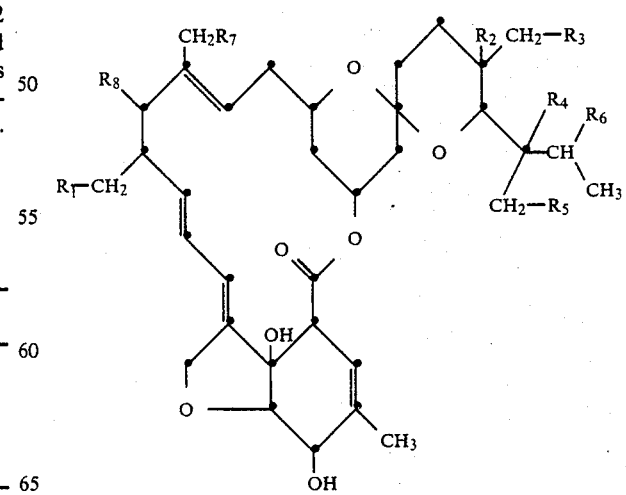

wherein $R_1$, $R_2$, $R_3$, $R_4$, $R_5$, $R_6$, $R_7$ and $R_8$ have the following meanings:

| $R_1$ | $R_2$ | $R_3$ | $R_4$ | $R_5$ | $R_6$ | $R_7$ | $R_8$ |
|---|---|---|---|---|---|---|---|
| OH | H | H | H | H | H | H | OH(epi) |
| H | H | H | H | H | H | OH | OH(epi) |
| H | H | OH | H | H | H | H | OH(epi) |
| H | H | H | OH | H | H | H | OH(epi) |
| H | H | H | H | H | OH | H | OH(epi) |
| OH | H | H | H | H | H | H | H |
| H | H | H | OH | H | H | H | H |
| H | H | H | H | OH | H | H | H |
| OH | H | OH | H | H | H | H | H |
| OH | H | H | OH | H | H | H | H |
| OH | H | H | H | OH | H | H | H |
| OH | H | H | H | H | OH | H | H |

11. A method for the treatment of insect, acarid and helminth infections in animals which comprises administering to an animal infected with such parasites an effective amount of a compound of claim 10.

12. A composition useful for the treatment of insect, acarid and helminth infections in animals which comprises an inert carrier and an effective amount of a compound of claim 10.

13. A compound having the formula:

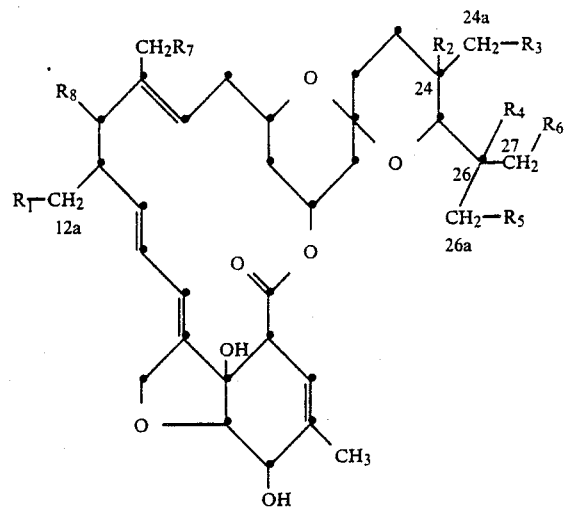

wherein $R_1$, $R_2$, $R_3$, $R_4$, $R_5$, $R_6$, $R_7$ and $R_8$ have the following meanings:

| $R_1$ | $R_2$ | $R_3$ | $R_4$ | $R_5$ | $R_6$ | $R_7$ | $R_8$ |
|---|---|---|---|---|---|---|---|
| OH | H | H | H | H | H | H | OH(epi) |
| H | H | H | OH | H | H | H | OH(epi) |
| H | H | H | H | H | OH | H | OH(epi) |
| OH | H | H | H | H | H | H | H |
| H | H | H | OH | H | H | H | H |
| H | H | H | H | H | OH | H | H |
| OH | H | H | OH | H | H | H | H |
| OH | H | H | H | H | OH | H | H |
| H | H | H | OH | H | H | OH | H |

14. A method for the treatment of insect, acarid and helminth infections in animals which comprises administering to an animal infected with such parasites an effective amount of a compound of claim 13.

15. A composition useful for the treatment of insect, acarid and helminth infections which comprises an inert carrier and an effective amount of a compound of claim 13.

* * * * *

UNITED STATES PATENT AND TRADEMARK OFFICE
CERTIFICATE OF CORRECTION

PATENT NO. : 4,666,937

DATED : May 19, 1987

INVENTOR(S) : R.T. Goegelman, E.S. Inamine, R.F. White

It is certified that error appears in the above-identified patent and that said Letters Patent is hereby corrected as shown below:

In Columns 5 and 6 in the table between lines 23 and 58, in compound 15 in said table, delete "12a,24" and insert therefor --12a,24a--

Signed and Sealed this

Seventeenth Day of May, 1988

Attest:

DONALD J. QUIGG

Attesting Officer

Commissioner of Patents and Trademarks